United States Patent
Pidgeon et al.

(10) Patent No.: US 6,579,720 B1
(45) Date of Patent: Jun. 17, 2003

(54) METHOD FOR ACTIVITY PROFILING COMPOUND MIXTURES

(75) Inventors: Charles Pidgeon, Cambridge, MA (US); Nadege M. Rooke, Framingham, MA (US); Jeffrey A. Ruell, Boston, MA (US)

(73) Assignee: BDC Pharma LLC, Chicago, IL (US)

( * ) Notice: Subject to any disclaimer, the term of this patent is extended or adjusted under 35 U.S.C. 154(b) by 0 days.

(21) Appl. No.: 09/569,427

(22) Filed: May 12, 2000

Related U.S. Application Data

(60) Provisional application No. 60/133,968, filed on May 13, 1999.

(51) Int. Cl.[7] .............................................. G01N 30/02
(52) U.S. Cl. ........................ 436/161; 435/7.1; 436/86; 436/164; 436/171; 436/173
(58) Field of Search ........................... 436/86, 161, 164, 436/171, 173; 435/7.1

(56) References Cited

U.S. PATENT DOCUMENTS

| | | | |
|---|---|---|---|
| 4,631,687 A | * | 12/1986 | Kowalski et al. |
| 5,756,994 A | | 5/1998 | Bajic |
| 5,766,481 A | * | 6/1998 | Zambias et al. |
| 5,993,662 A | * | 11/1999 | Garr et al. |
| 6,080,318 A | * | 6/2000 | Gumm et al. |
| 6,355,163 B2 | * | 3/2002 | Hindsgaul et al. |

FOREIGN PATENT DOCUMENTS

| | | | |
|---|---|---|---|
| WO | WO 99/10522 | | 3/1999 |
| WO | WO 00/29848 | * | 5/2000 |

OTHER PUBLICATIONS

"A Method for Quantitatively Differentiating Crude Natural Extracts Using High–Performance Liquid Chromatography–Electrospray Mass Spectrometry" by R.K. Julian, R.E. Higgs, J.D. Gygl, and M.D. Hilton, Anal. Chem. (1998) vol. 70, 3249–3254.

"A Chemical Screening Strategy for the Dereplication and Prioritization of HIV–Inhibitory Aqueous Natural Products Extracts" by J.H. Cardellina, M.H.G. Munro, R.W. Fuller, K.P. Manfredi, T.C. McKee, M. Tischler, H.R. Bokesch, K.R. Gustafson, J.A. Beutler, and M.R. Boyd, Journal of Natural Products (1993) vol. 56, No. 7, 1123–1129.

* cited by examiner

*Primary Examiner*—Jan Ludlow
(74) *Attorney, Agent, or Firm*—Barnes & Thornburg

(57) ABSTRACT

A method is described for identifying compounds in a complex mixture exhibiting a predetermined characteristic. The mixture is separated into fractions using at least two unique sets of separation parameters to produce at least two series of separation parameter dependent fractions. In one embodiment the mixtures are separated chromatographically using unique sets of separation parameters and the fractions are analyzed spectroscopically to provide data indicative of the component compounds and the fractions are analyzed in synchronously combined fractions, for the predetermined characteristic. The spectroscopic data for the fractions exhibiting the predetermined characteristic are compared to identify compound(s) common to the fractions exhibiting the characteristic. The method can be implemented in an automatic chromatographic system to provide rapid screening of complex compound mixtures for predetermined chemical or biological characteristics and to identify those components of the mixture exhibiting such characteristics.

14 Claims, 26 Drawing Sheets

Example of Algorithm

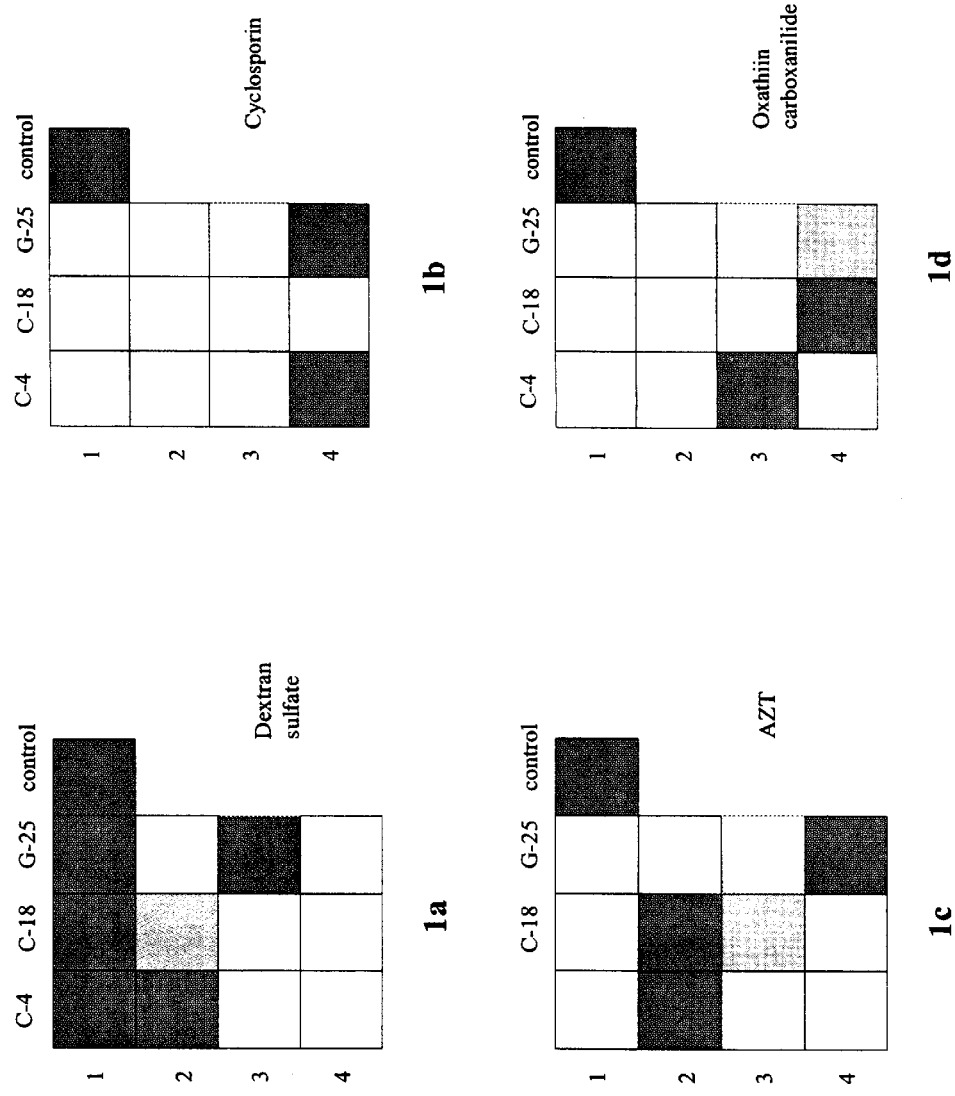
Figure 1. Boyd's chemical screening patterns of HIV-inhibitory standards

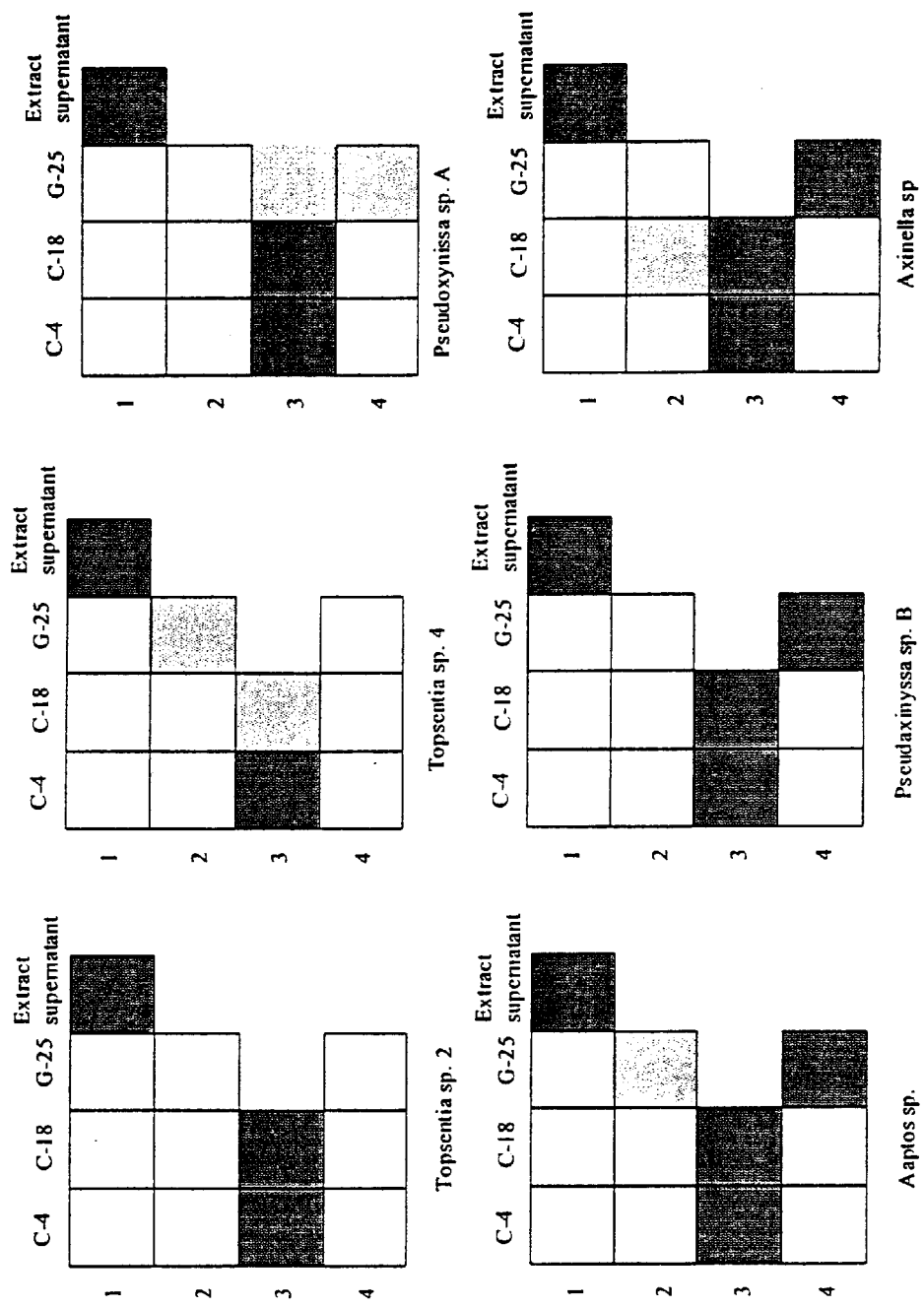
Figure 2. Boyd's chemical screening patterns of sponge extract

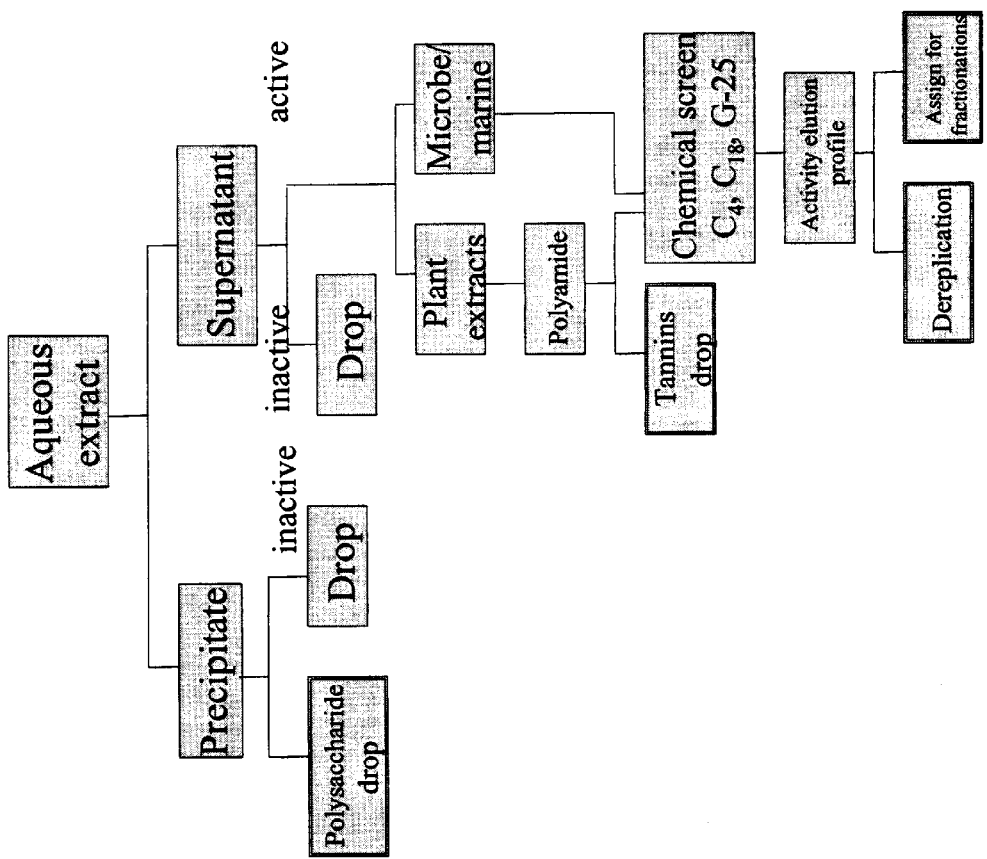
Figure 3. Boyd's dereplication strategy

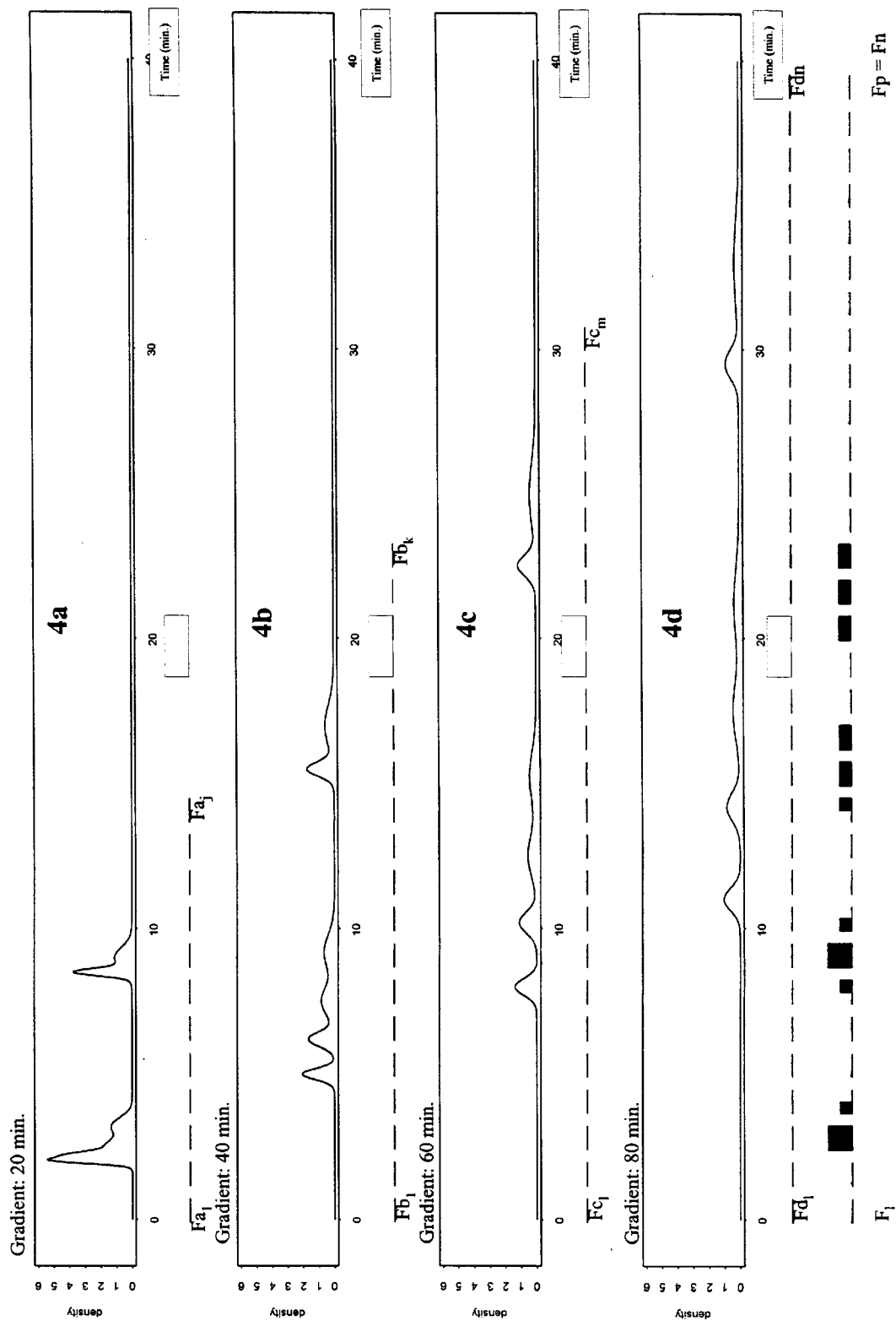

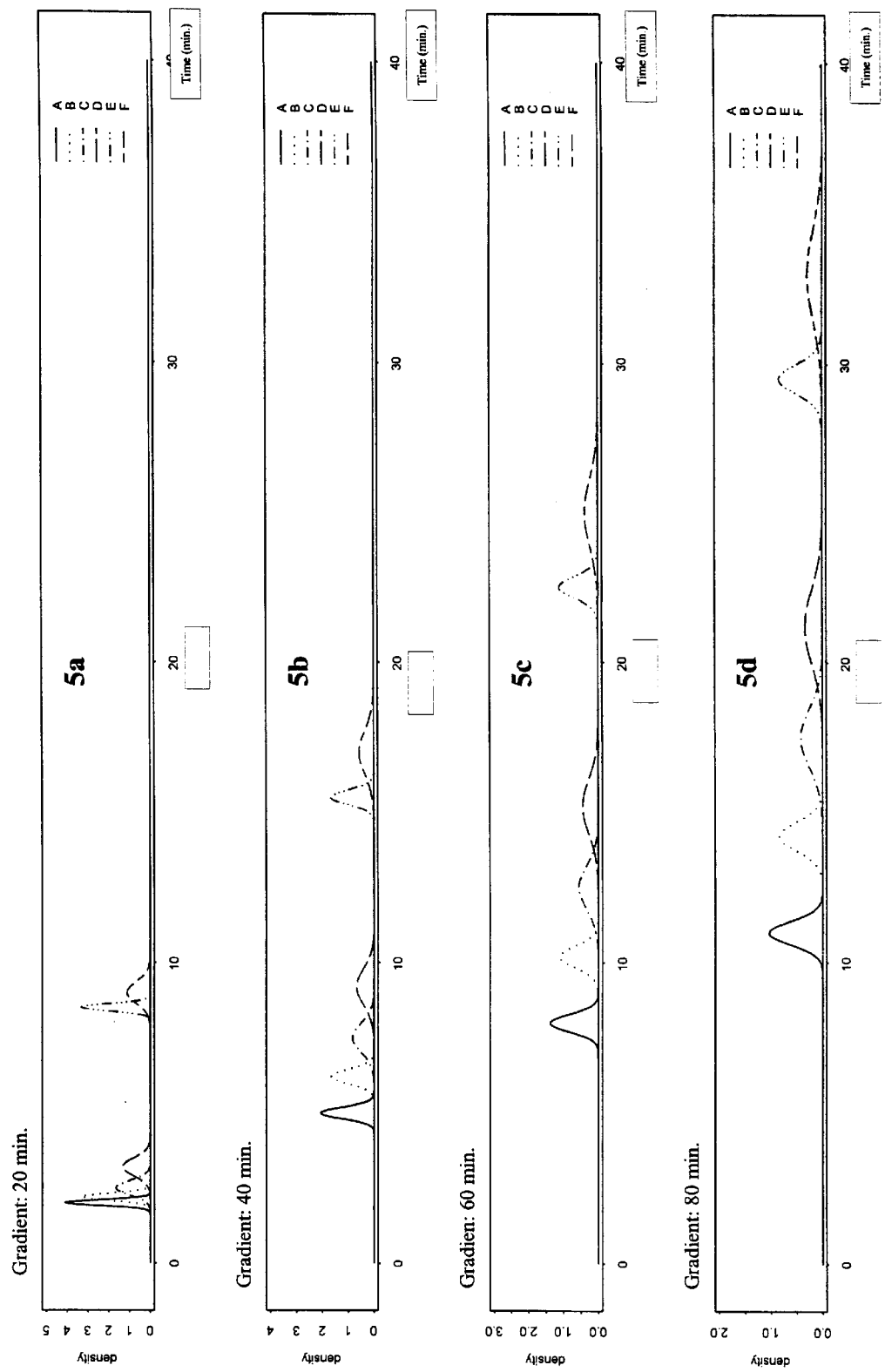
Figure 5. Individual elution profiles

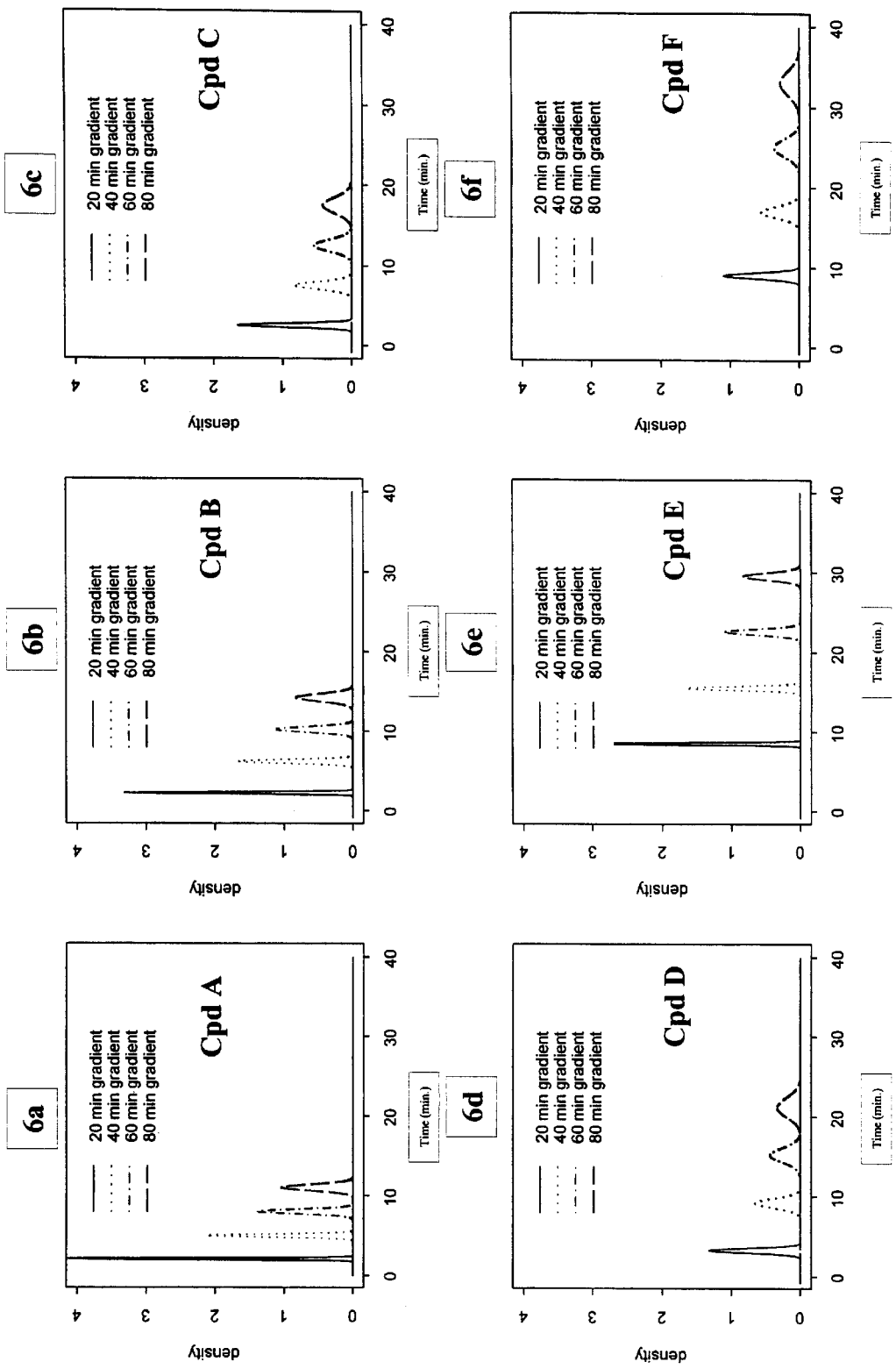
Figure 6. Chromatographic fingerprints of compounds A-F

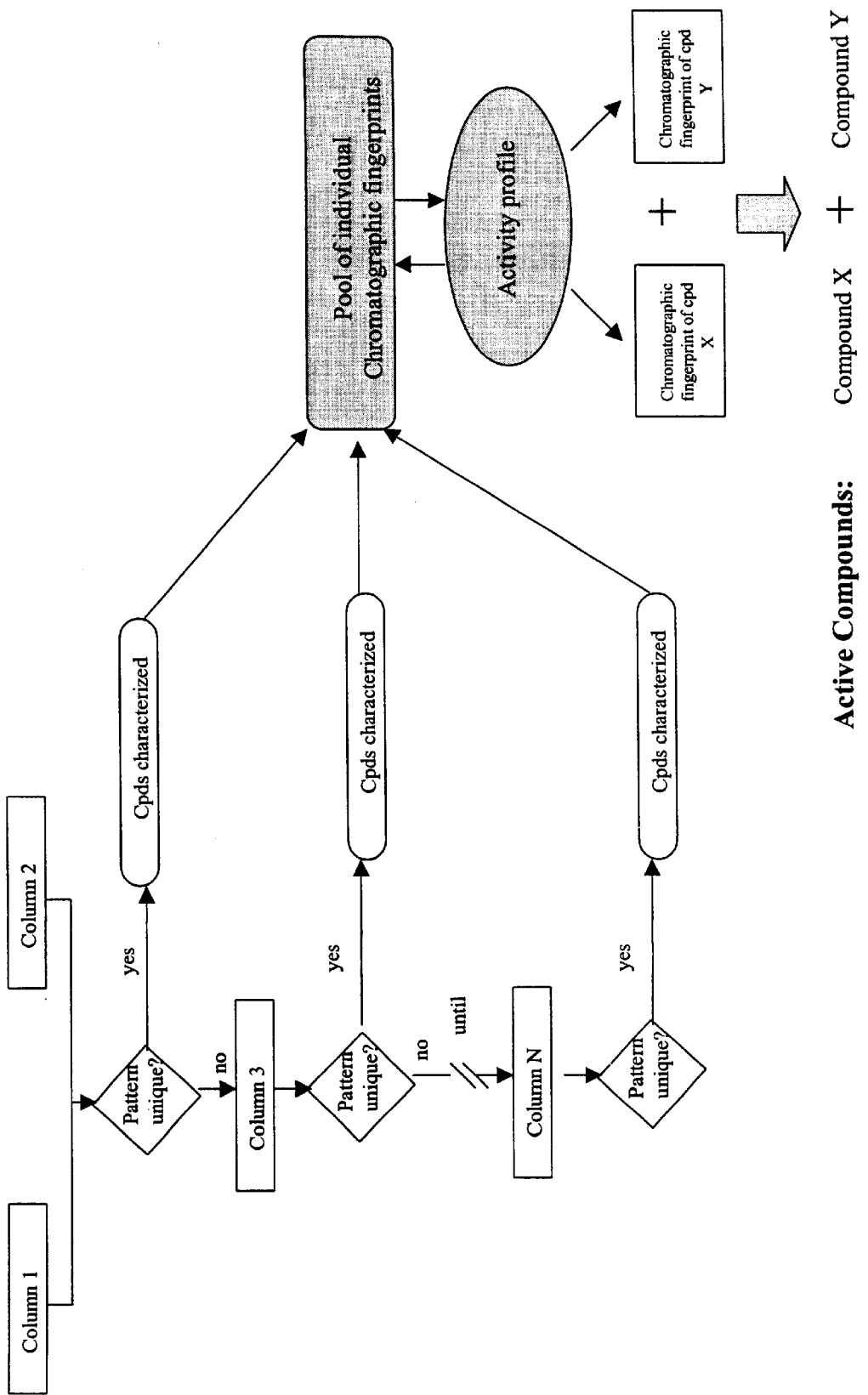
Figure 7. Example of Algorithm

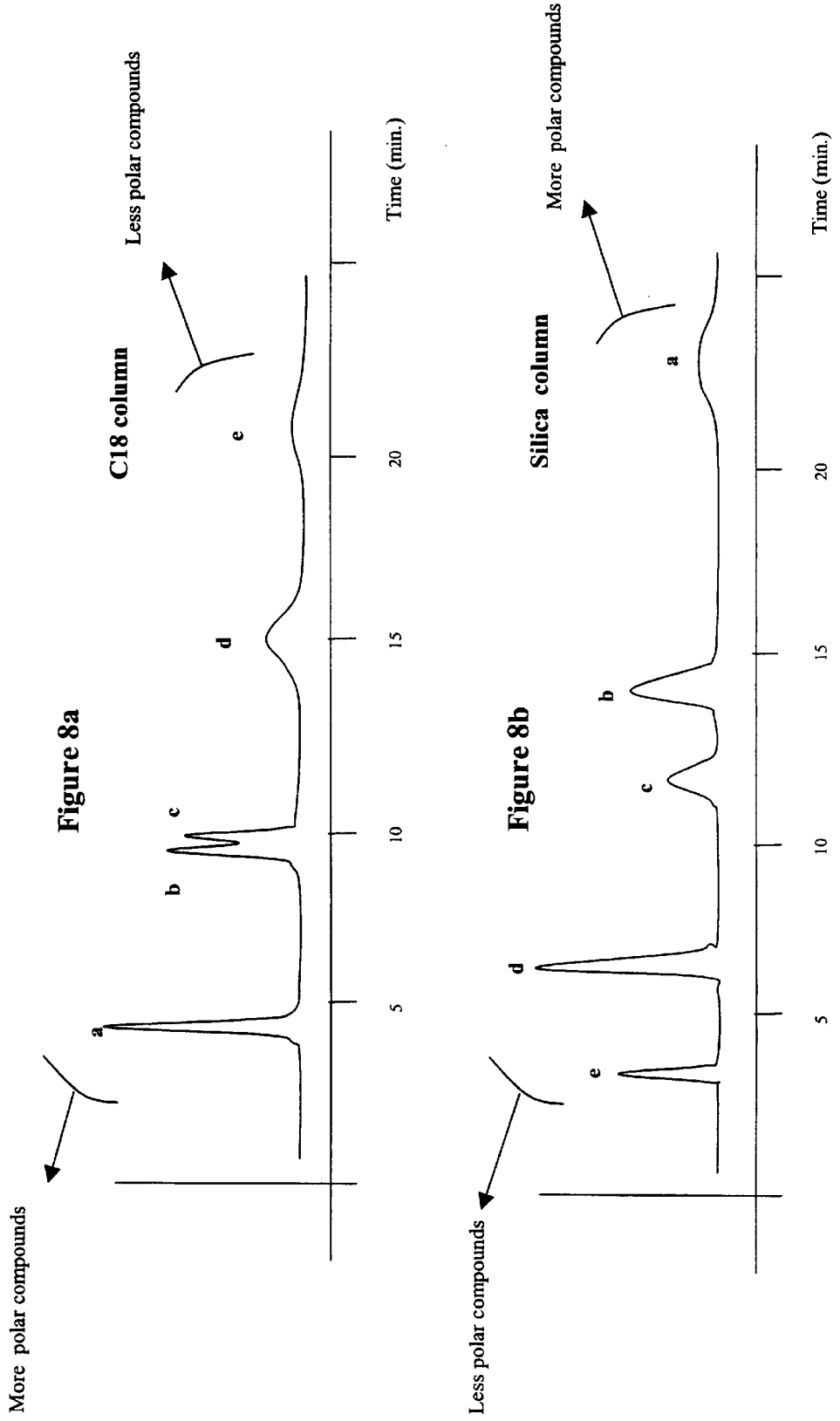
Figure 8. Simulated elution order reversal of a compound mixture on C18 (8a) and Silica (8b) columns

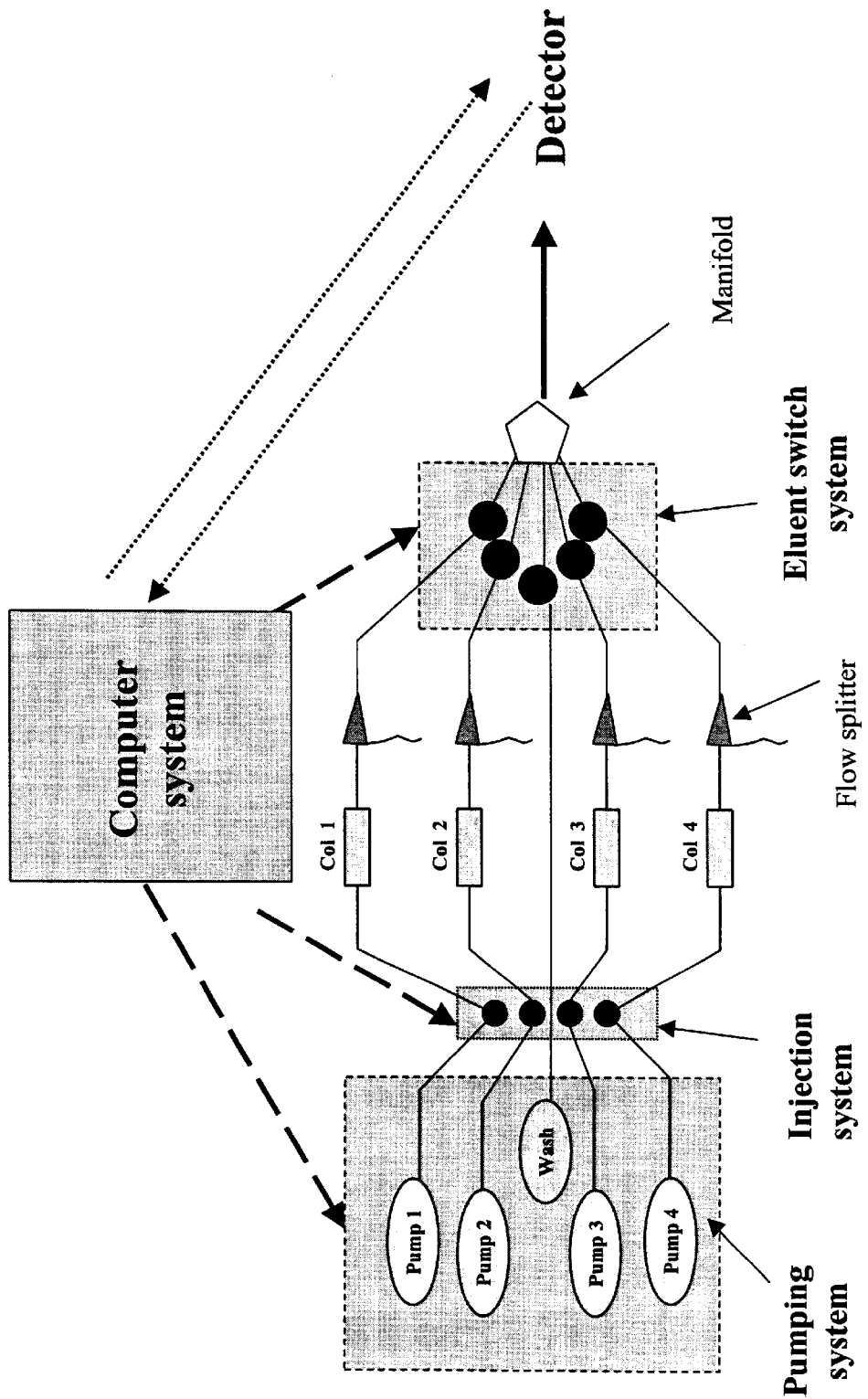
Figure 9. Eluent switch interfaced LC/MS system

Figure 10a and 10b. Instrumental set up and flow gradient profile
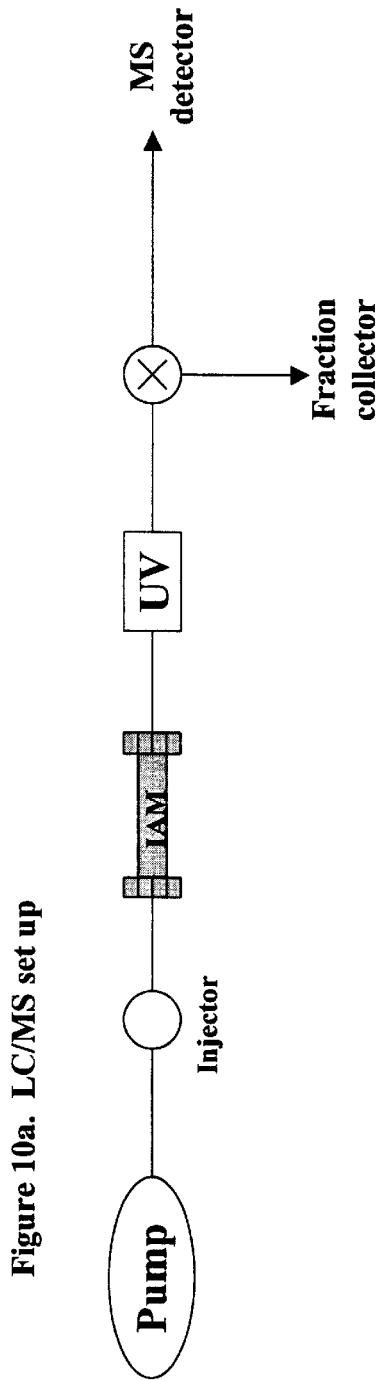
Figure 10a. LC/MS set up
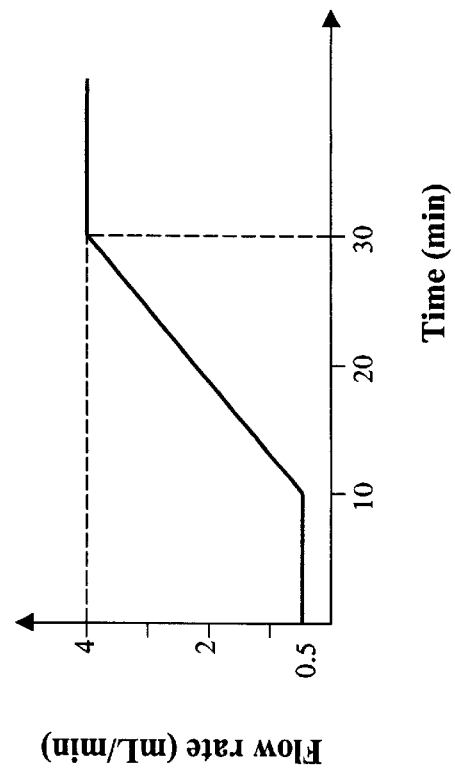
Figure 10b. Flow gradient profile

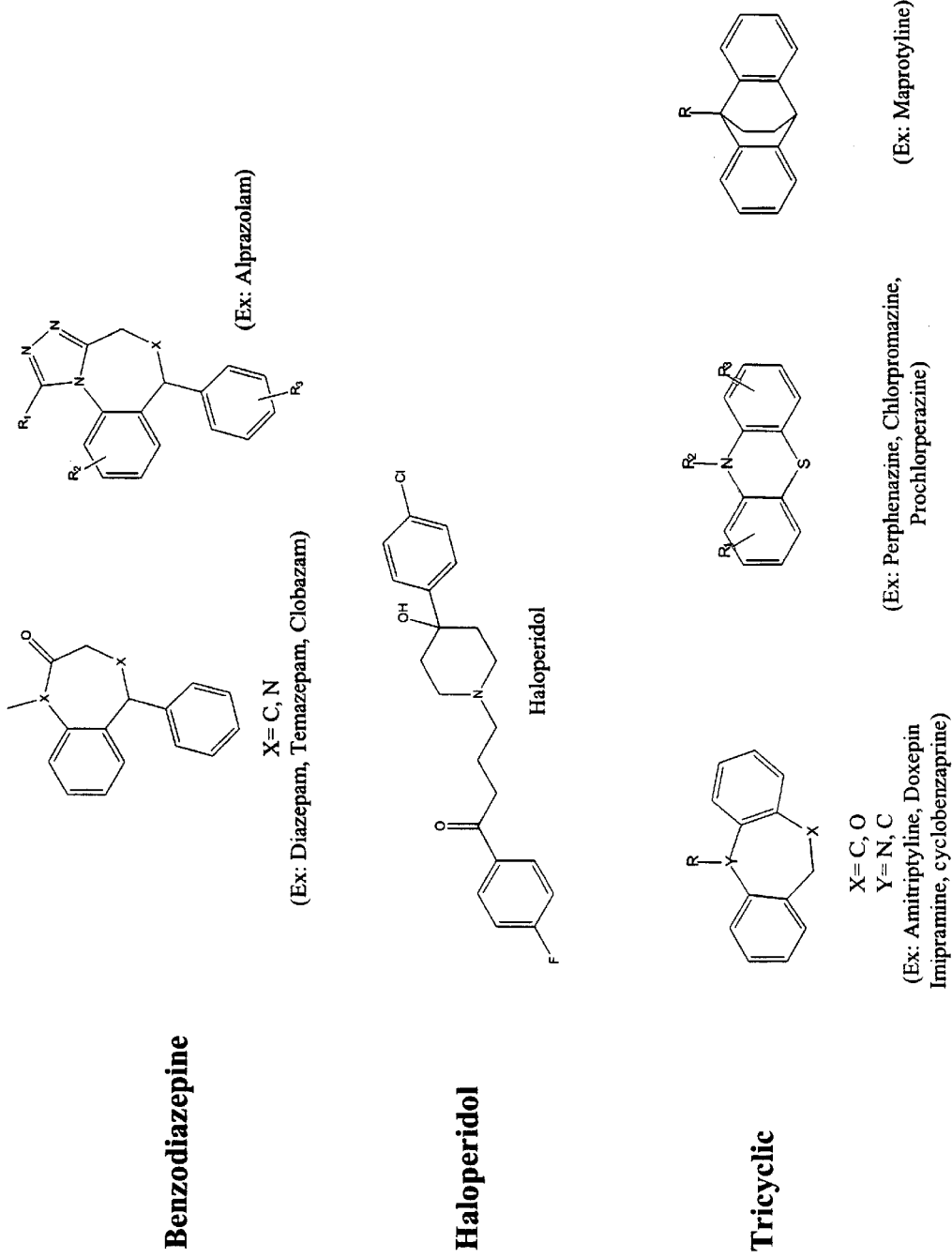
Figure 11. Structural features for positive ELISA tests

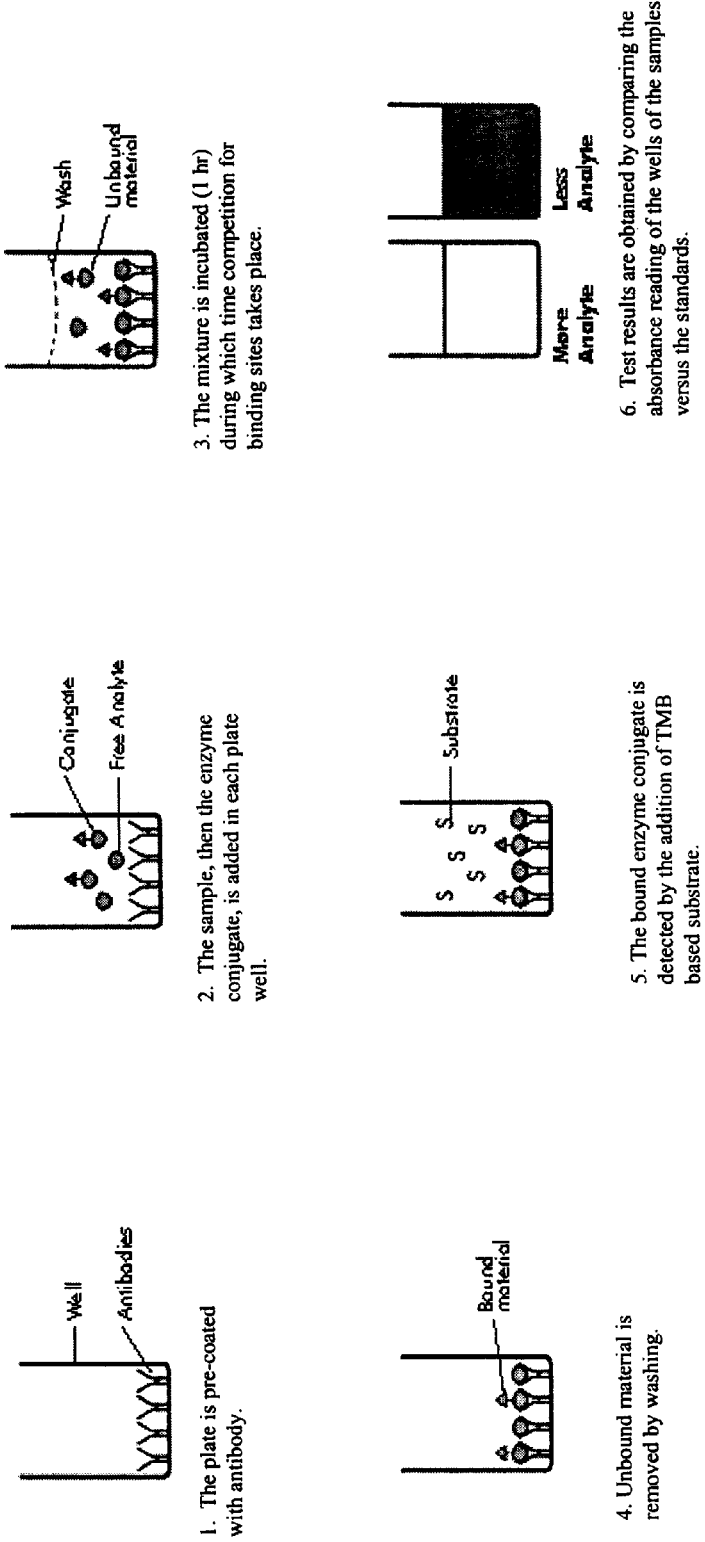
Figure 12. ELISA Assay Principle

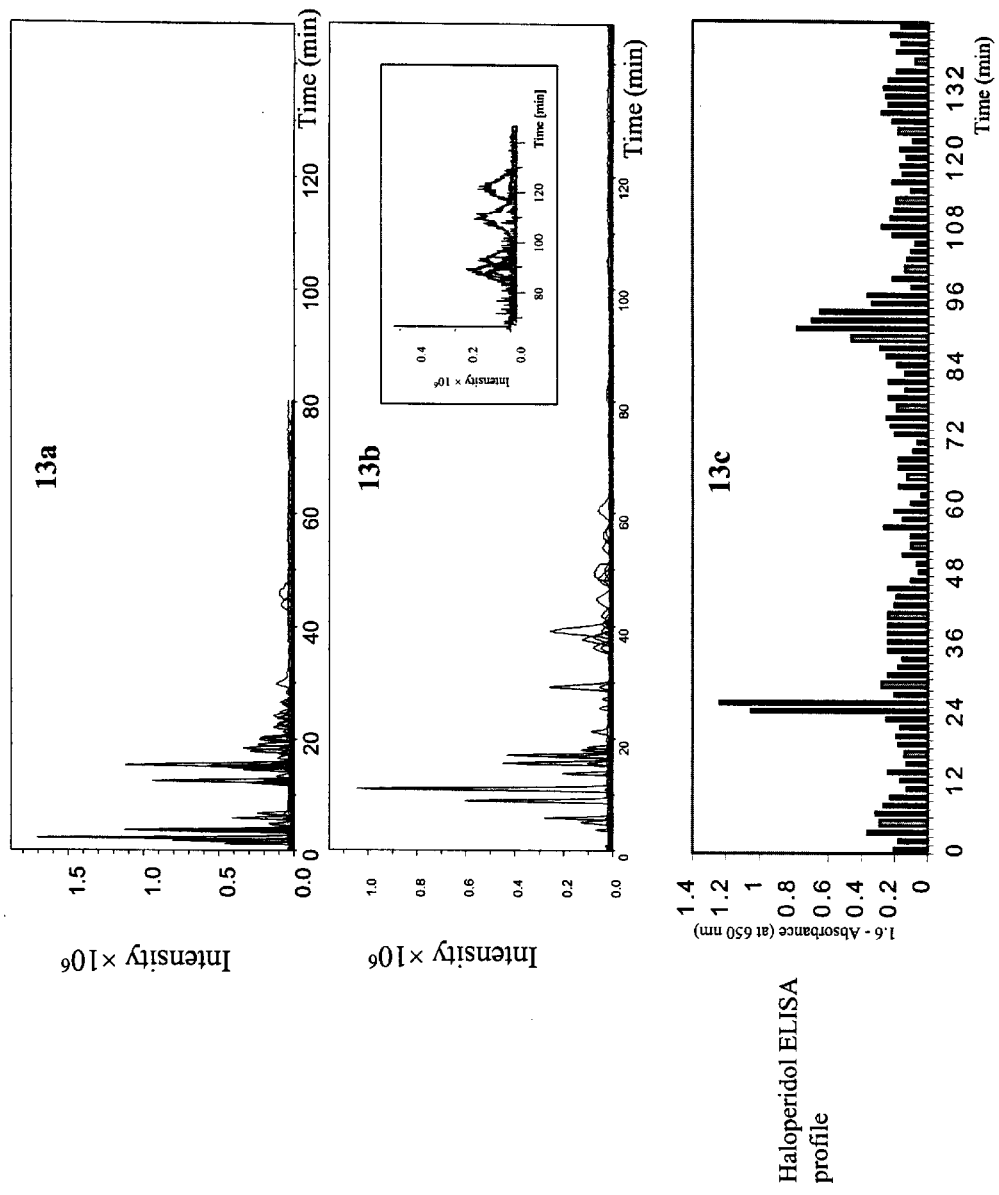
Figure 13. Total Ion chromatograms generated from loading a complex mixture of 70 compounds on either $^{ester}$IAM.PE$^{C10/C3}$ (13a) or $^{ester}$IAM.PS$^{C10/C3}$ columns (13b)

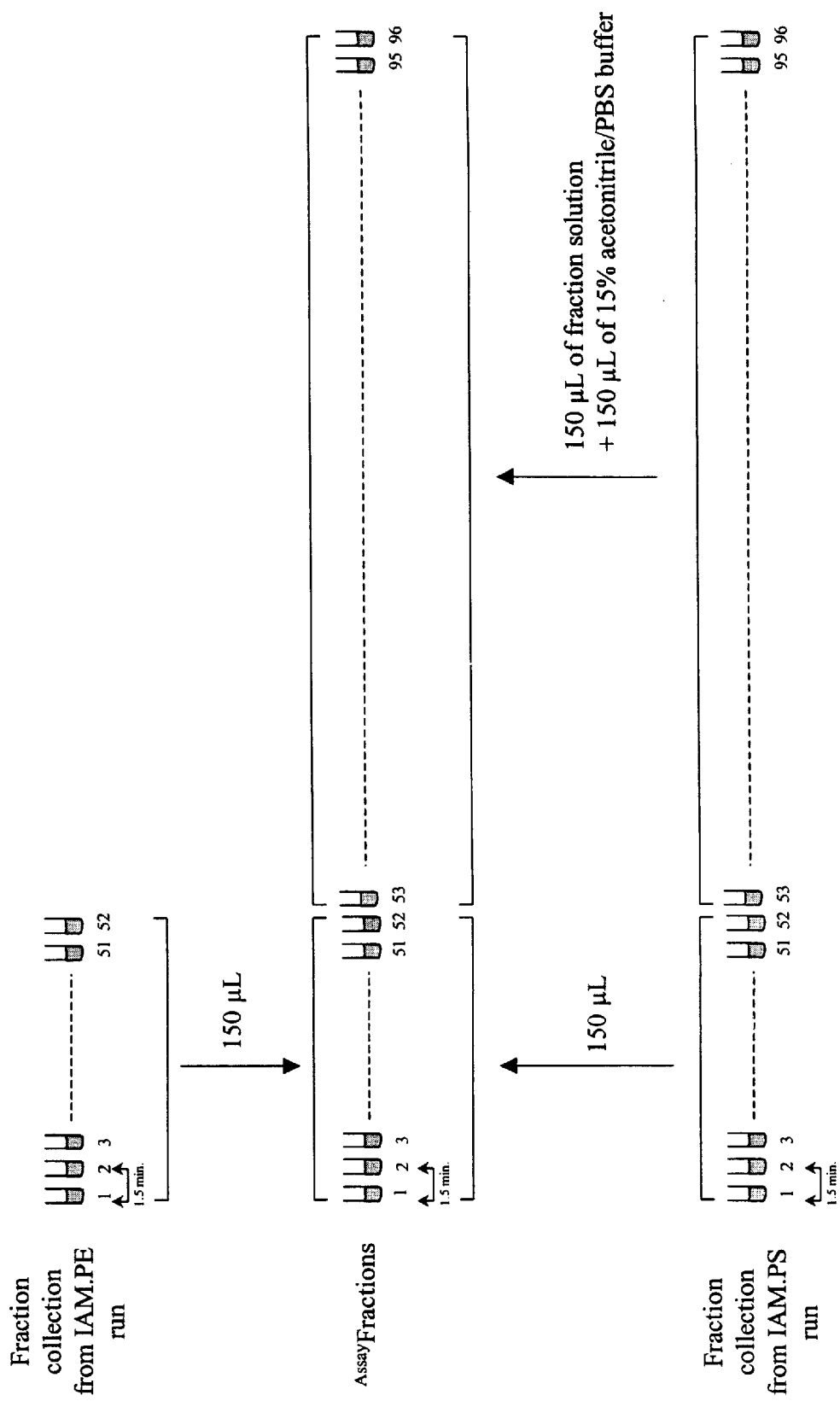
Figure 14. Fraction collection and combination for activity profiling

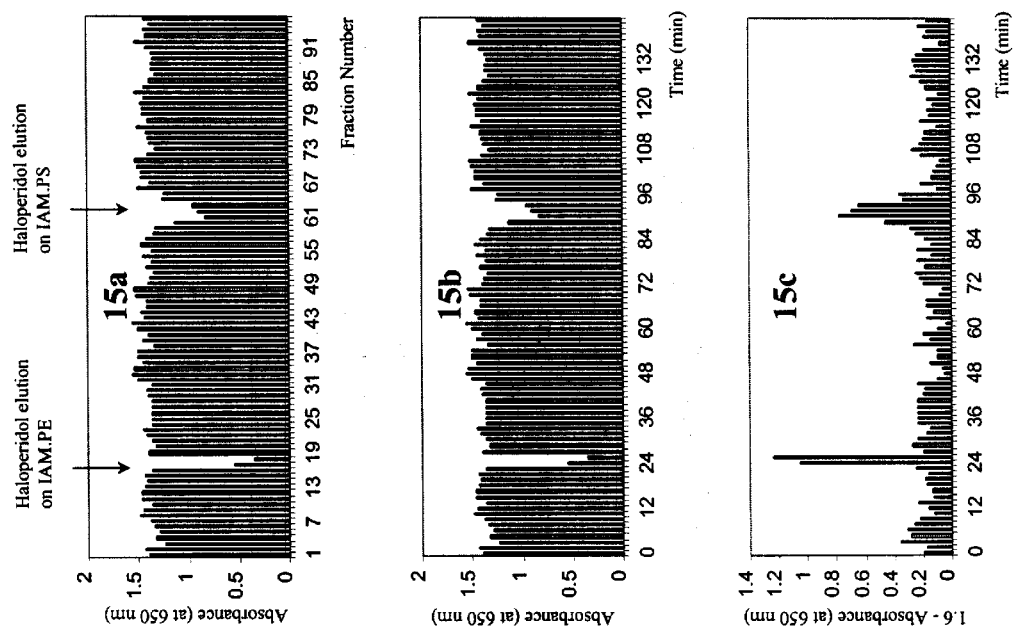
Figure 15. Haloperidol ELISA experiment results

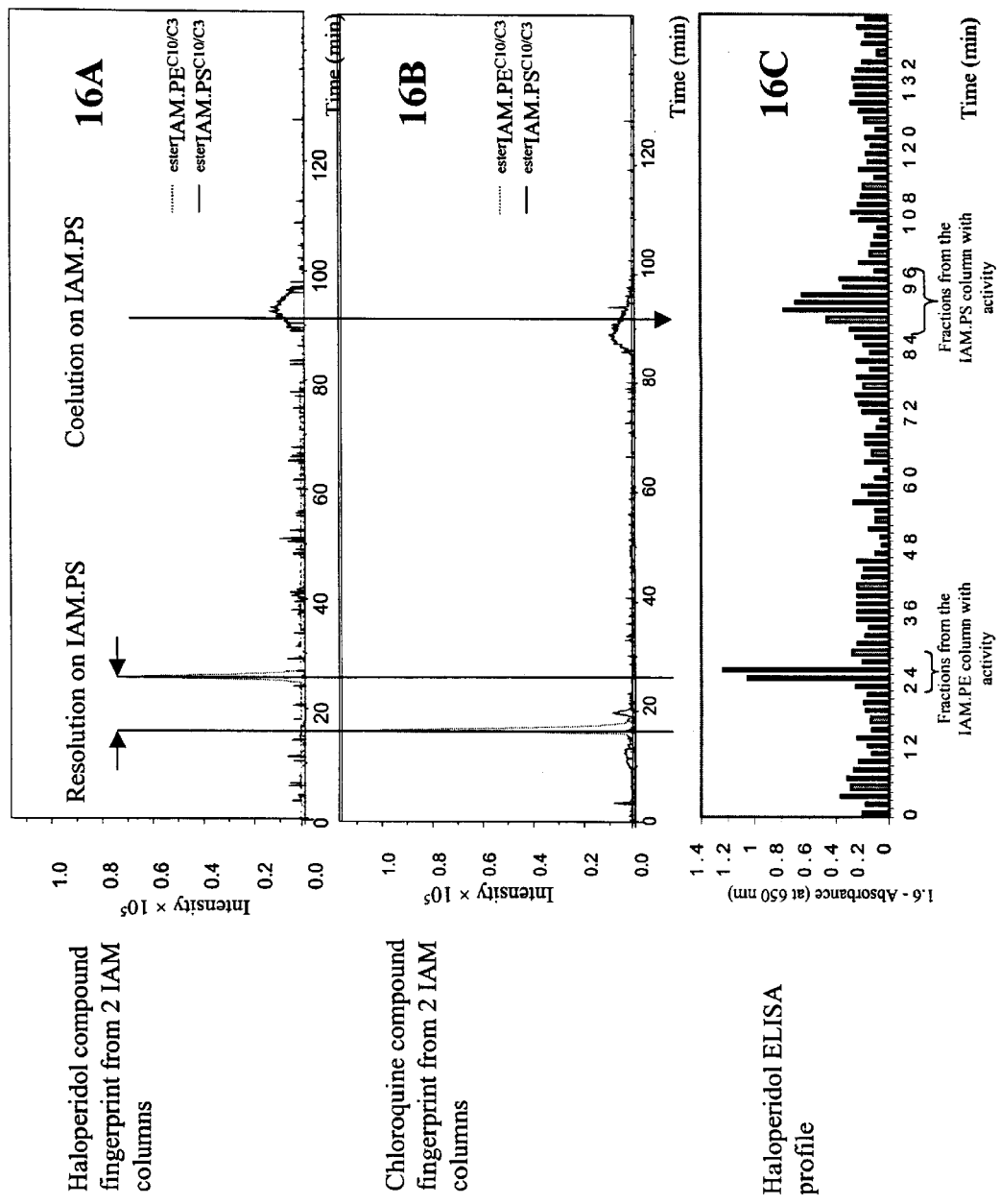
Figure 16. Resolution of Haloperidol (16A) with Chloroquine (16B) on an esterIAM.PE^{C10/C3} column, but not on an esterIAM.PS^{C10/C3} column

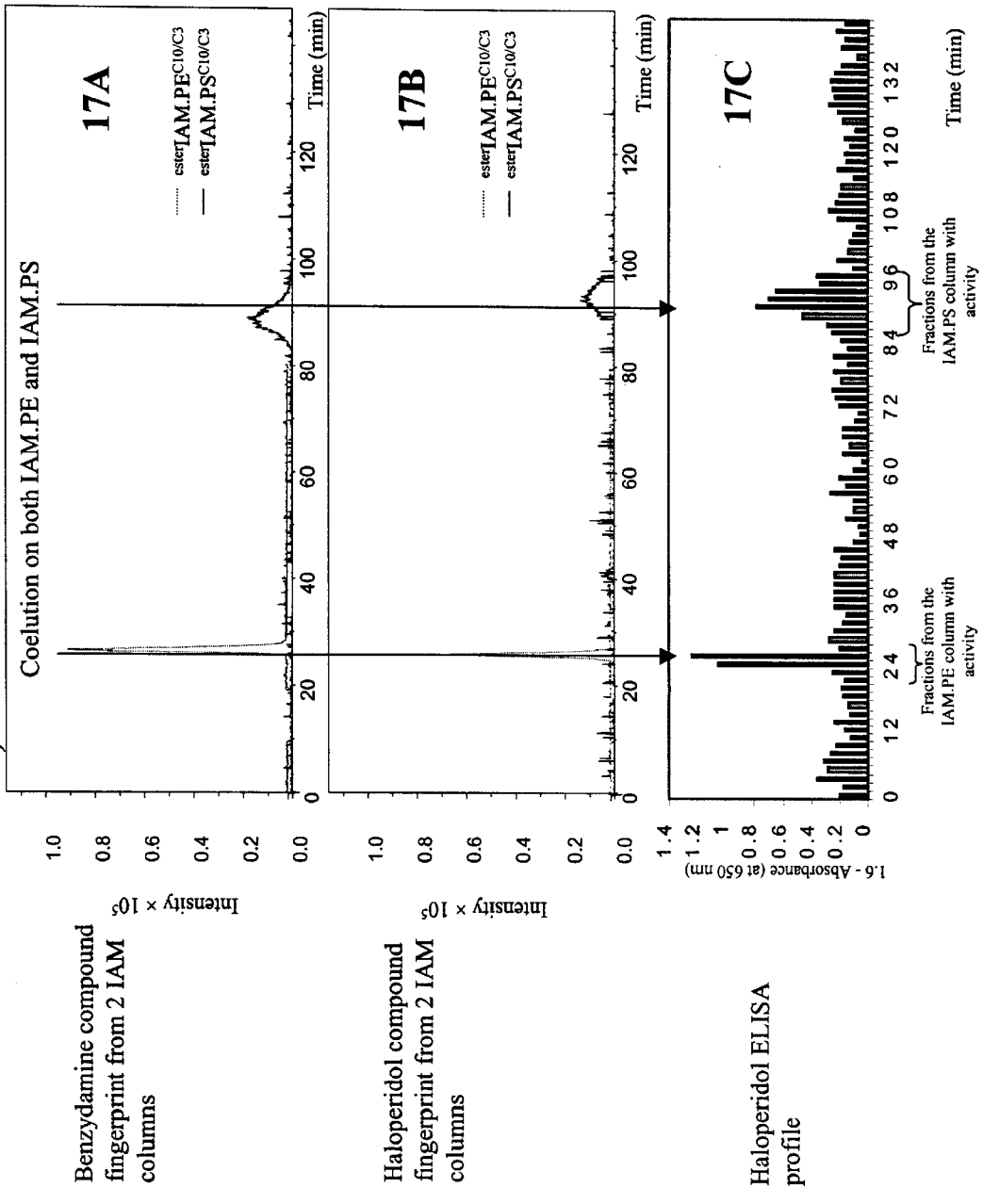
Figure 17. Co-elution of Benzydamine (17A) with Haloperidol (17B) on an esterIAM.PE$^{C10/C3}$ column, but not on an esterIAM.PS$^{C10/C3}$ column

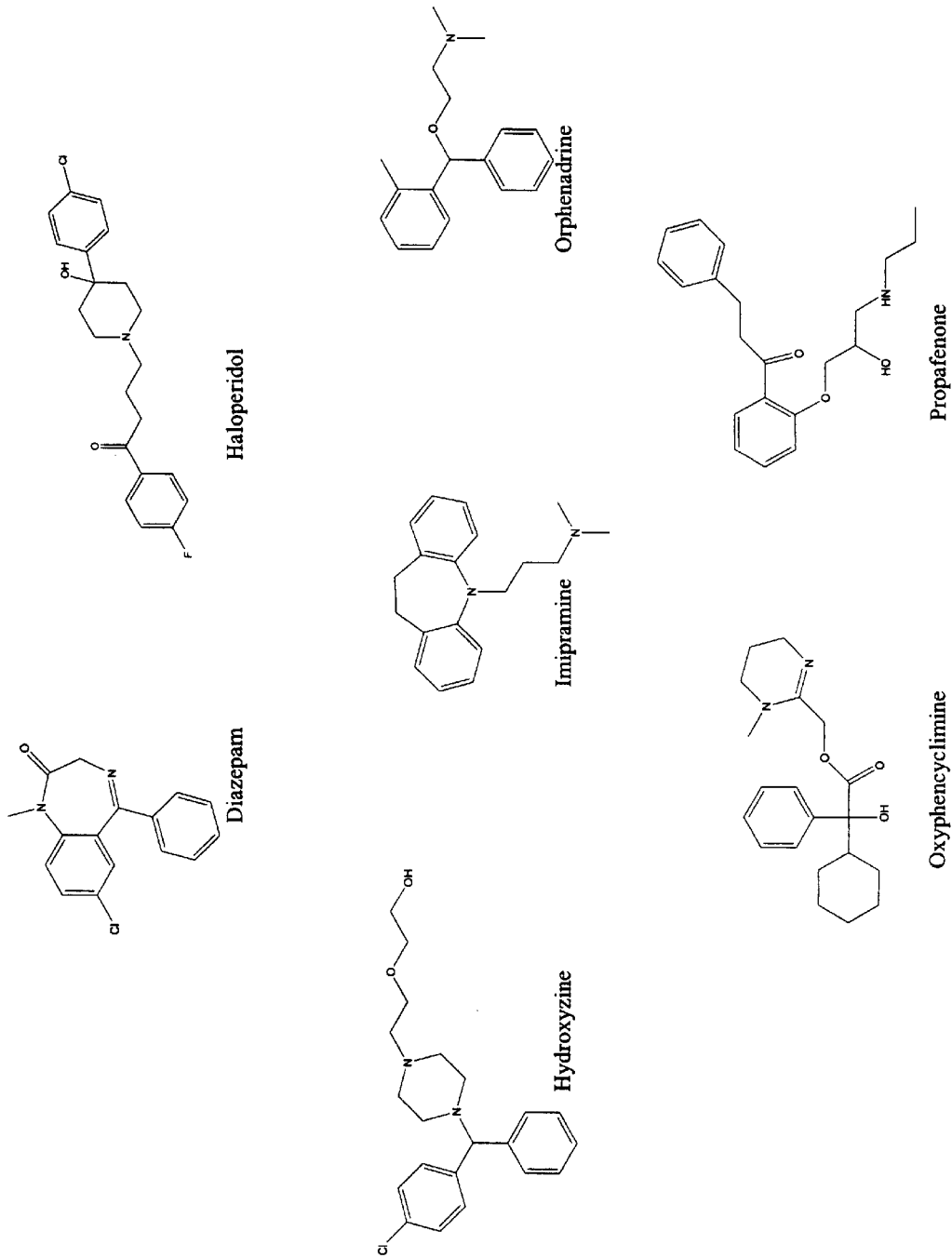
Figure 18. Chemical structures of test compounds

Figure 19. Elution order of Diazepam, Haloperidol, Hydroxyzine, Imipramine, Orphenadrine, Oxyphencyclimine, and Propafenone on IAM.PE and IAM.PS columns
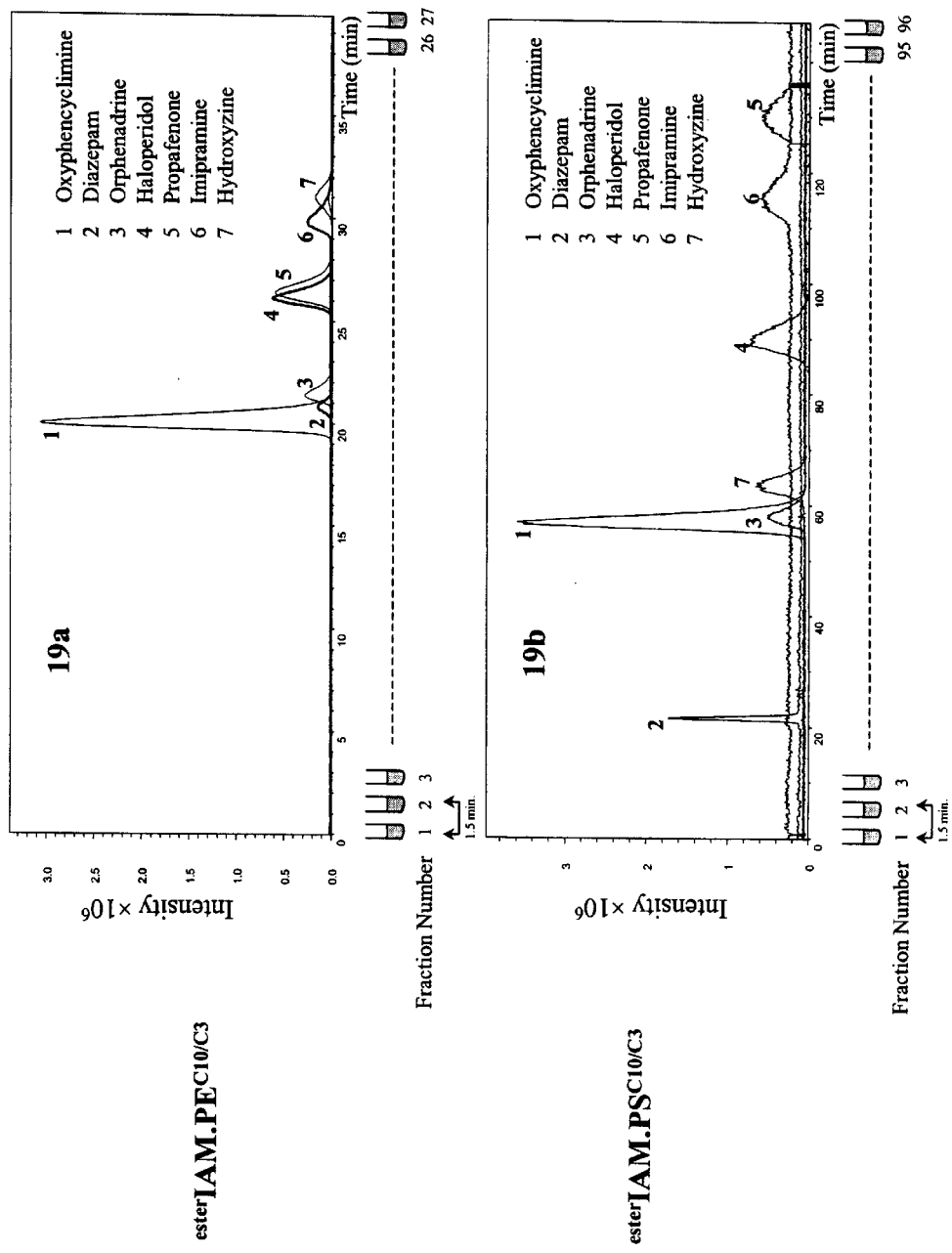

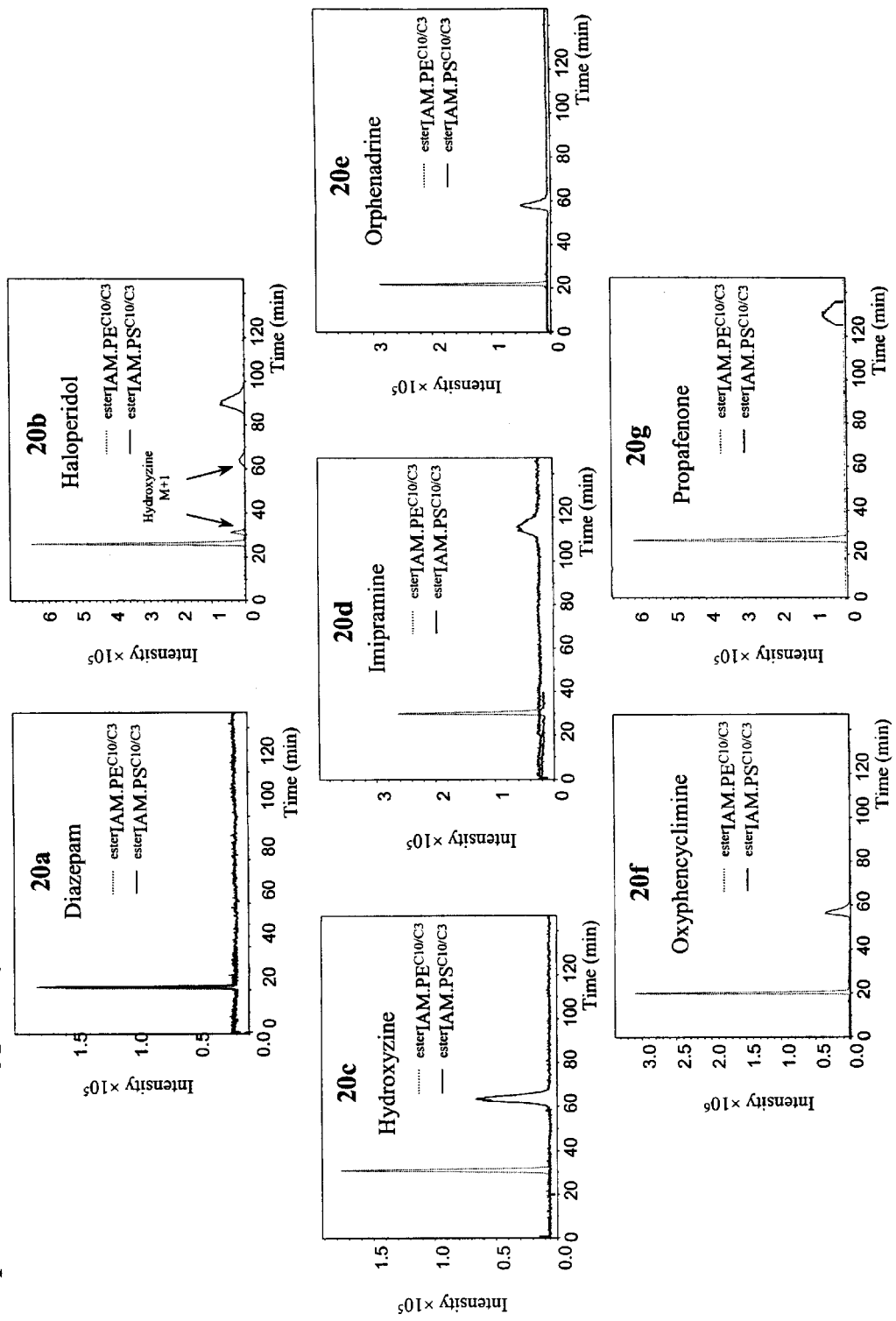
Figure 20. Chromatographic fingerprints of Diazepam, Haloperidol, Hydroxyzine, Imipramine, Orphenadrine, Oxyphencyclimine, and Propafenone on IAM.PE and IAM.PS columns

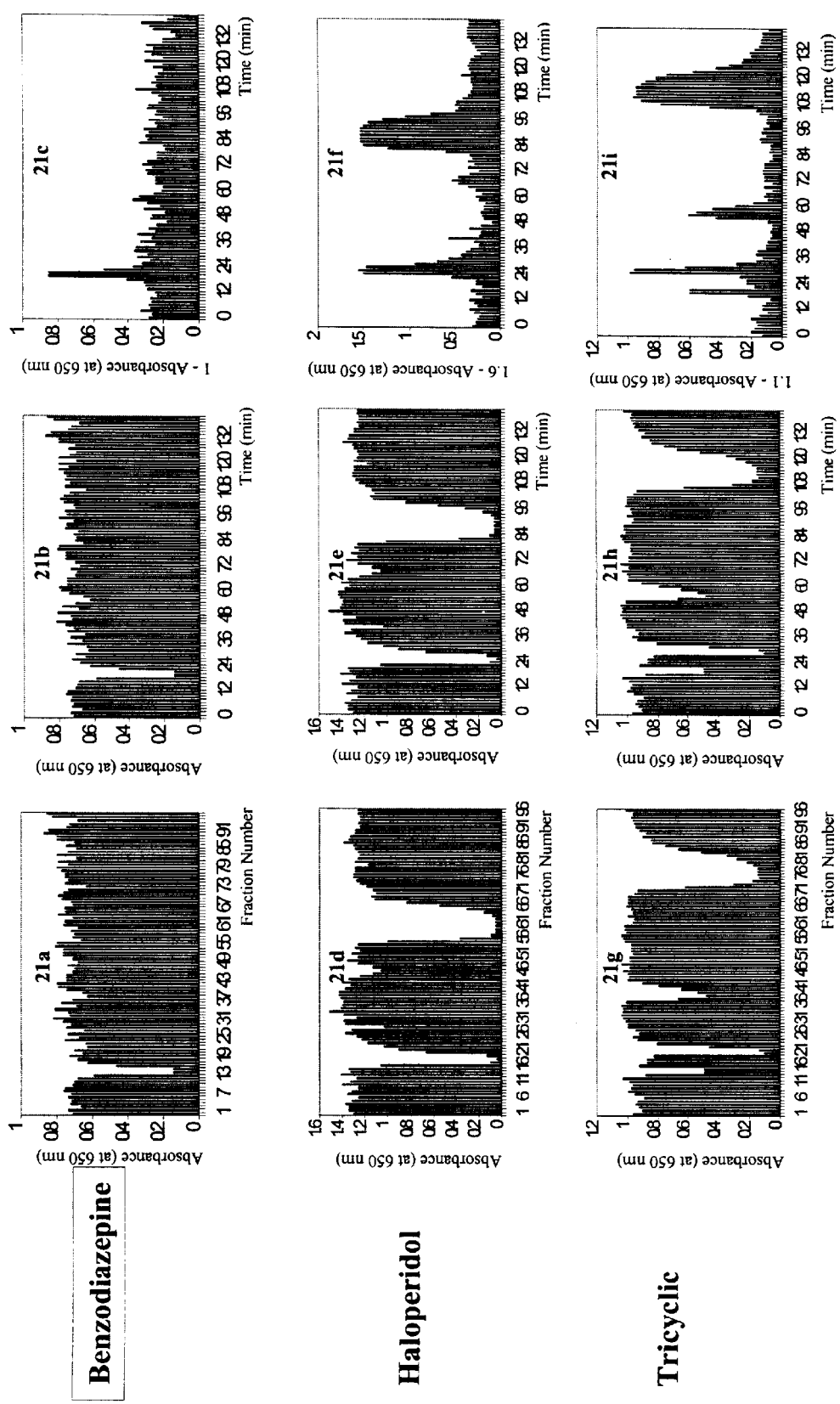
Figure 21. results from the Benzodiazepine, Haloperidol, and tricyclic ELISA assays

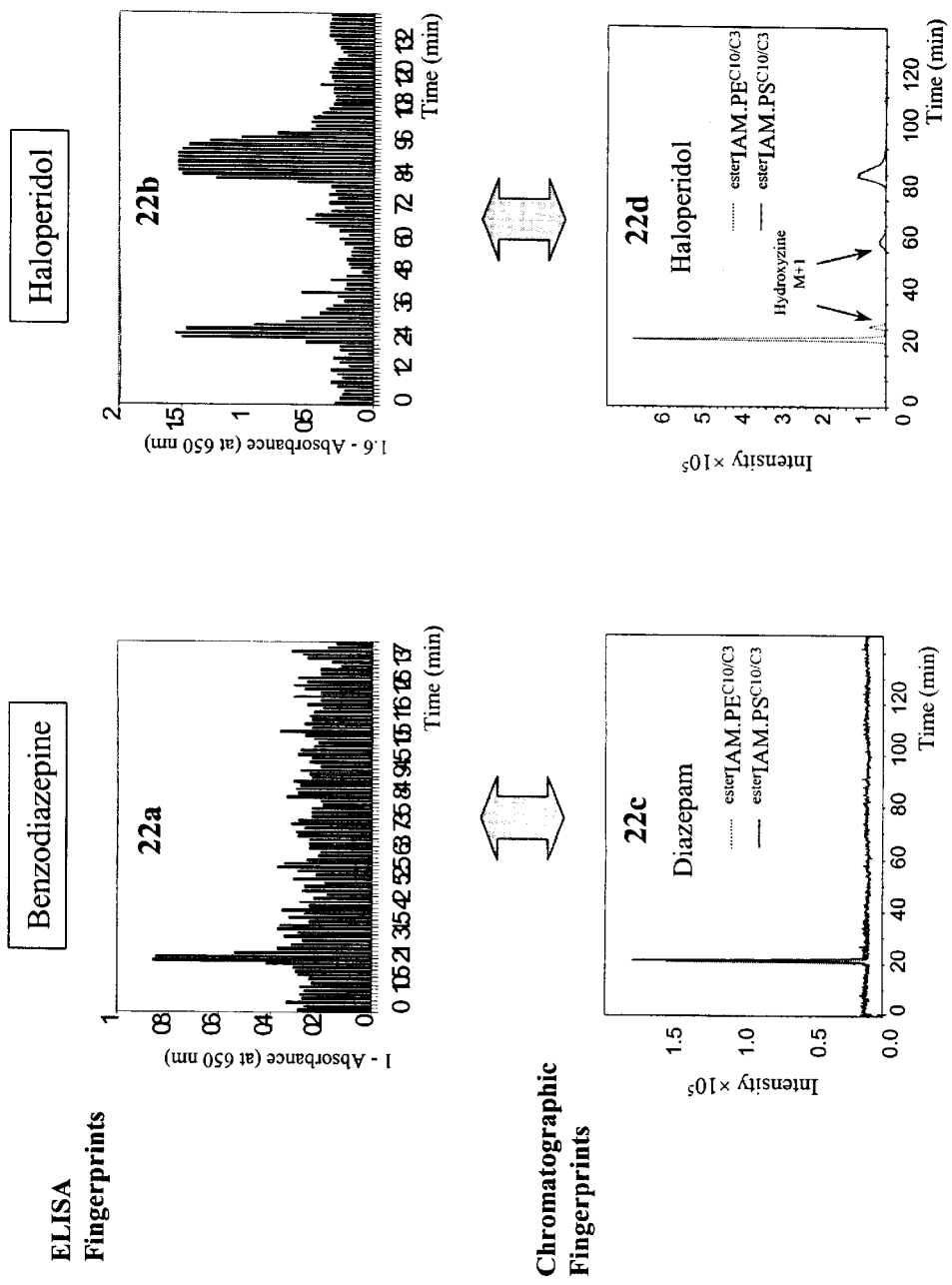
Figure 22. Fingerprint match between the Benzodiazepine and Haloperidol ELISA profiles and the two-separation-parameter-chromatographic profiles of Diazepam and Haloperidol respectively Figure 23. Deconvolution of the Tricyclic ELISA Assay
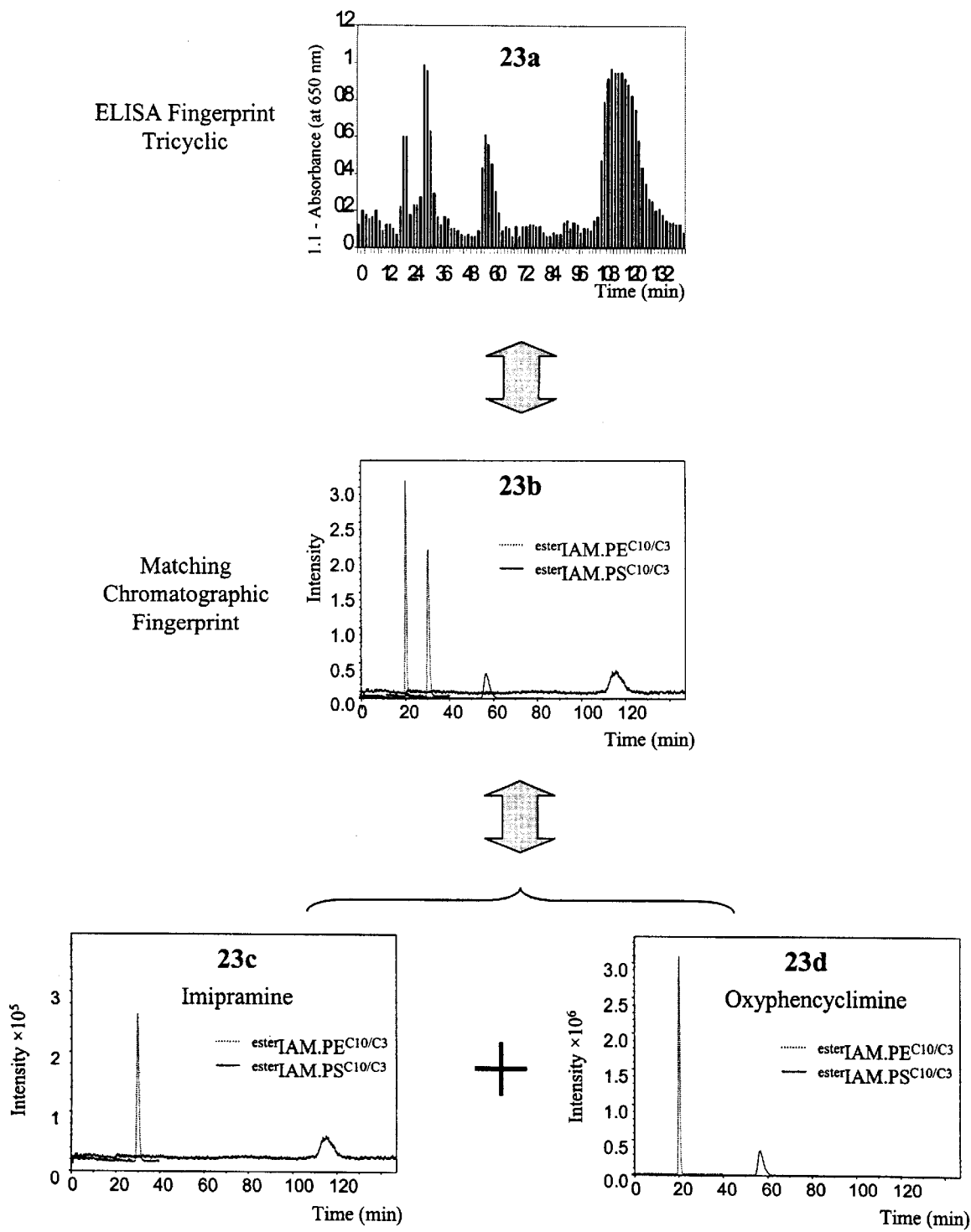

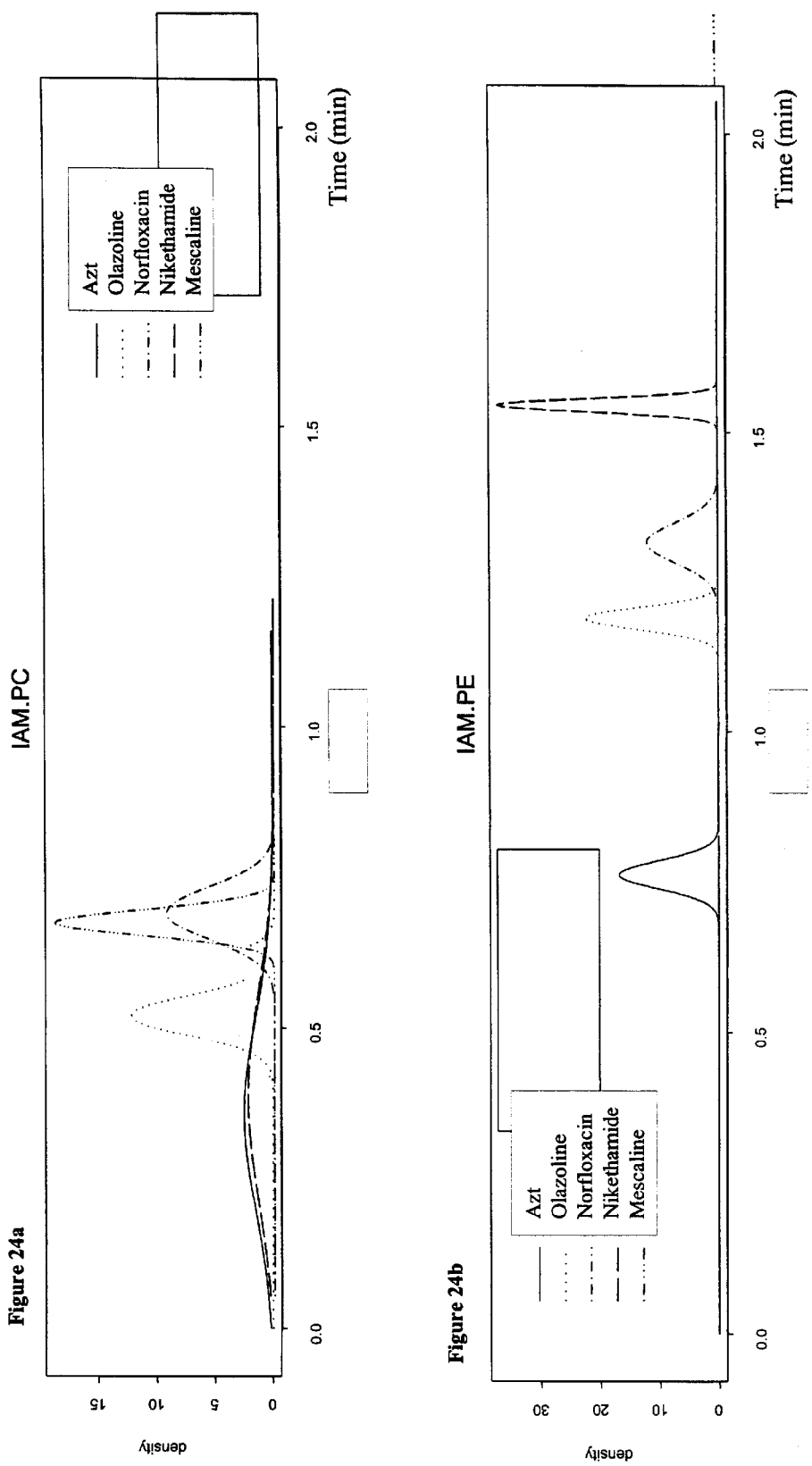
Figure 24a and 24b. Elution order of Azt, Olazoline, Norfloxacin, Nikethamide, and mescaline on IAM.PC and IAM.PE columns

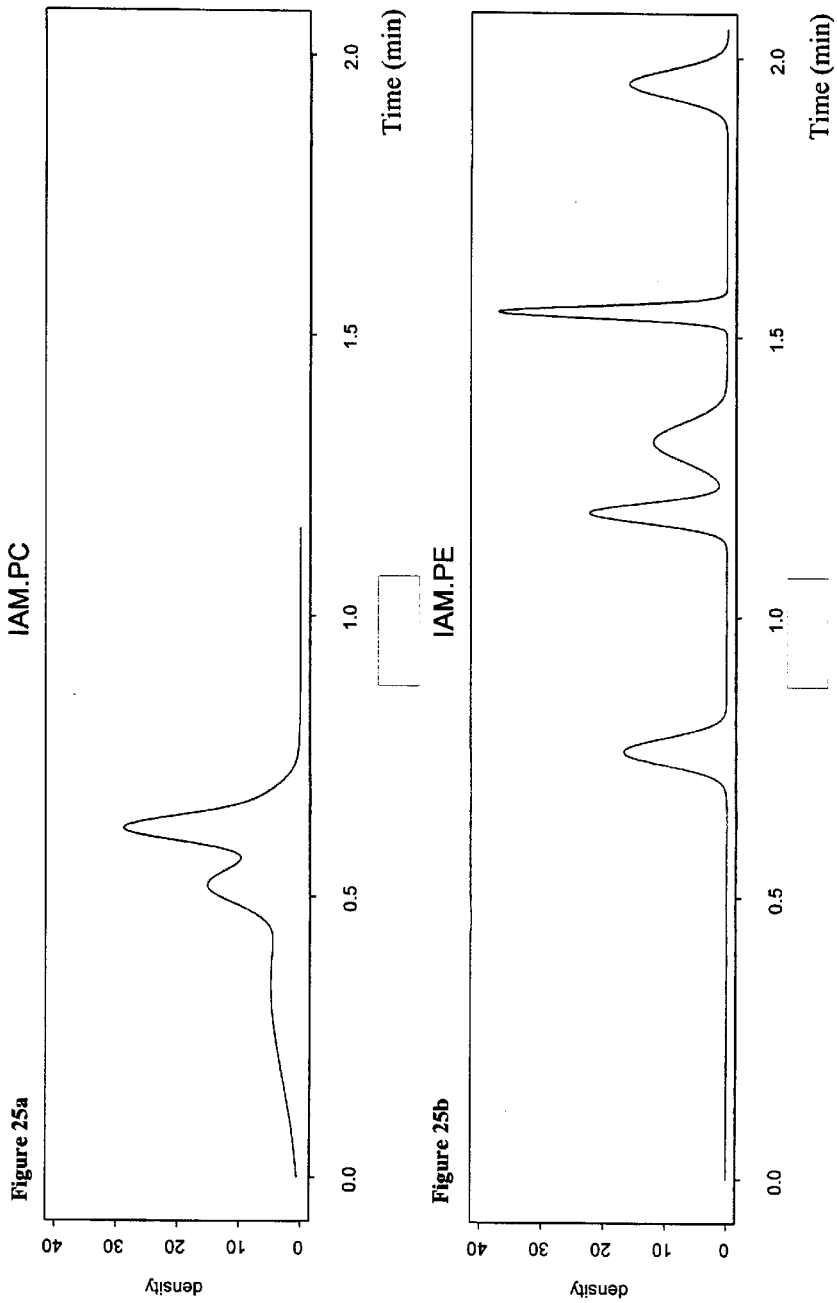
Figures 25a and 25b. Expected chromatographic profiles of AZT, Olazoline, Norfloxacin, Nikethamide and Mescaline on IAM.PC and IAM.PE columns respectively

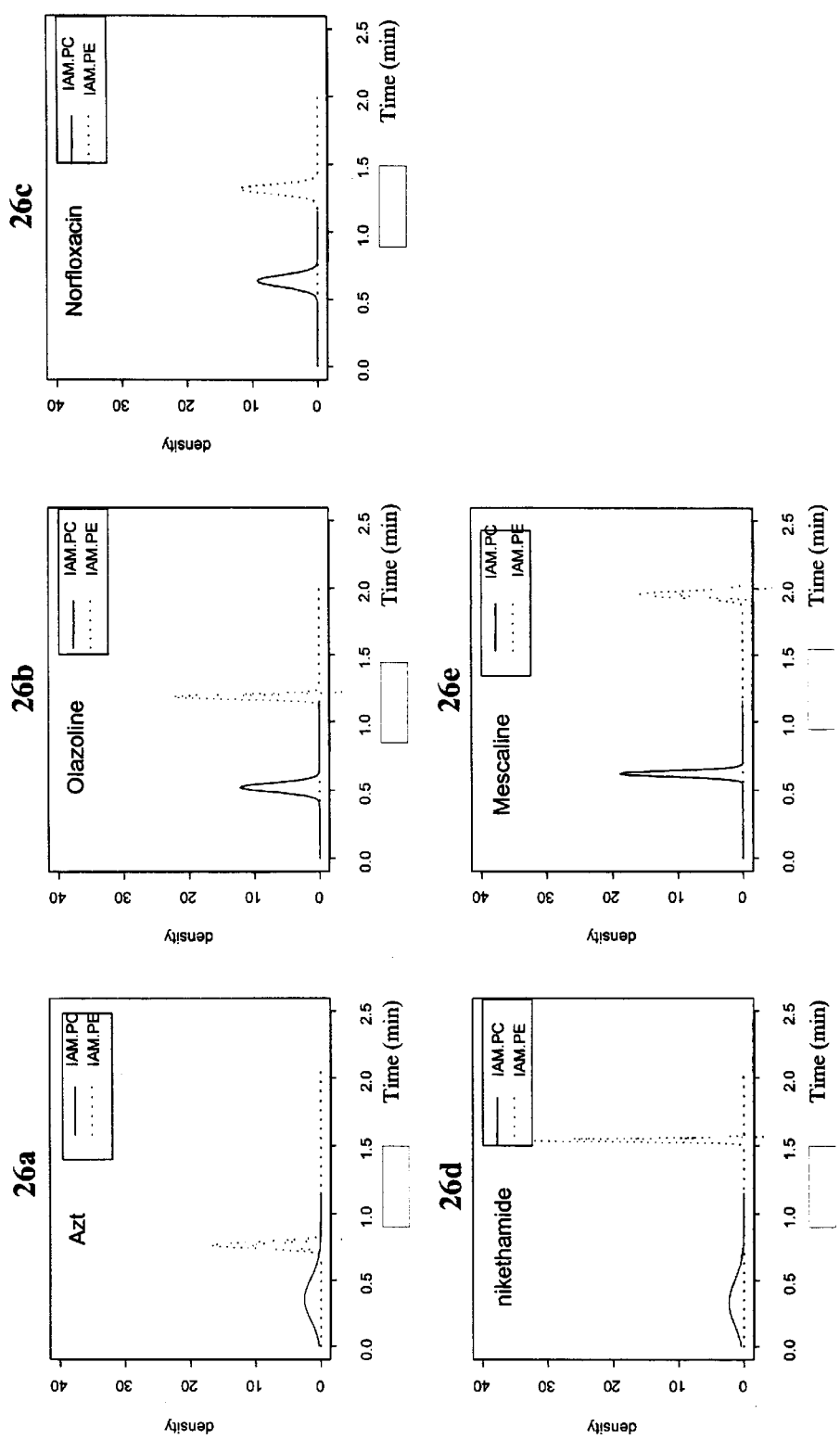
Figure 26. Chromatographic fingerprints of AZT, Olazoline, Norfloxacin, Nikethamide, and Mescaline using IAM.PC and IAM.PE columns

METHOD FOR ACTIVITY PROFILING COMPOUND MIXTURES

CROSS-REFERENCE TO RELATED APPLICATION

This application claims priority to U.S. Provisional Application Serial No. 60/133,968, filed May 13, 1999.

FIELD OF THE INVENTION

This invention relates to a method for analyzing complex mixtures of compounds. More particularly, the present invention is directed to a high efficiency method for screening a complex mixture of compounds for a predetermined characteristic, such as a chemical or biological property, and identifying the compounds in the mixture exhibiting said characteristic.

BACKGROUND AND SUMMARY OF THE INVENTION

The emergence of automated chemical synthesis platforms coupled with combinatorial techniques as a routine tool in the pharmaceutical industry that has enabled the synthesis of large numbers of compounds in a relatively short time. Millions of potential new drug candidates are synthesized every year, and both pharmaceutical and biotechnology industries have embraced the challenge in recent years of developing new, faster and more efficient ways to screen pharmaceutical compounds in order to rapidly identify "hits" and develop them into promising lead candidates.

The development of a chemical lead into an ideal marketable medicine requires a balance in potency, safety, and pharmacokinetics. The overall cost of bringing a new medicine to the market place is very high: recent surveys indicate that the average new chemical entity taken to market in the United States requires 10 to 15 years of research and costs more than $300 million. The major reasons for failure in development often involve clinically unacceptable kinetics, bioavailability or toxicity and the need for uncovering this information at earlier (less costly) stages of the drug discovery process is evident. Thus, there is a significant need to develop methods for rapidly evaluating these properties, as well as the bioactivity potential, for the ever-increasing number of compounds generated by combinatorial chemistry. Analytical researchers have turned their attention to development of high-throughput analytical approaches. Chromatographic systems have been developed and specifically designed for automated high-throughput identification, purity assessment, purification and biological screening of combinatorial libraries. In parallel to this, a great deal of research effort has been devoted to the optimization of screening assays to meet the requirements of high throughput screening. In theory, any assay performed on the bench top can be applied in HTS (High Throughput Screening), but the adaptation of such assays to an automated format may not be straightforward and often requires modifications of the assay to circumvent constraints imposed by HTS. The ideal assay is one that can be performed in a single well with no other manipulation other than the addition of the sample to be tested. A number of assay formats have been developed or modified over the past few years to conform to the constraints imposed by HTS, particularly emphasizing automation, and miniaturization.

The technological advances directed toward the implementation of fast and high volume chromatographic systems have rapidly converged toward automated systems for accommodating the large number of compounds typically produced in parallel syntheses. Despite recent developments of rapid and efficient methods for high throughput screening, intense efforts are ongoing to create new, more economical and more efficient methods for carrying out screening processes.

A few methods addressing the need for more efficient screening techniques have emerged over the past few years. Recently, a chemical-screening scouting technique for preliminary chemical characterization for natural product extracts was used for the dereplication and prioritization of HIV-inhibitory aqueous natural product extracts by Boyd M. R. et al., "A Chemical Screening Strategy for the Dereplication (elimination from further consideration) and Prioritization of HIV-Inhibitory Aqueous Natural Products Extracts", *J. Nat. Prod.*, 1993, 56, No 7, pp 1123–1129). The method is based on a preliminary chemical characterization, or "chemical screening", of natural product extracts by performing a series of chromatographic separations on different columns addressing distinct chemical/physicochemical properties of the solutes. For example, Sephadex G-25 cartridges were utilized first to provide information about molecular size and weight. Bonded-phase cartridge, $C_4$ wide pore (300 Å) and $C_{18}$ narrow pore (60 Å), were utilized to determine the relative polarity of active constituents. Four fractions were collected from each cartridge; they were tested side by side with the parent supernatant for anti-HIV activity. Thus, a distinctive or characteristic chromatographic profile of the active constituents was obtained, along with information about the recovery of activity and, by inference, the stability of the active compounds. This chemical-screening approach was first validated with a number of HIV-inhibitory standards, e.g., AZT, Dextrin sulfate, Cyclosporin, and Oxathiin carboxanilide. As illustrated in FIG. 1, different patterns of elution were observed for each compound tested. The recurring patterns of bioactivity elution could be readily discerned from the matrix form shown. Similarly, several sponge extracts were evaluated for the elution pattern in the chemical screen (FIG. 2).

The chemical-screening approach was used to gain insight into the general chemical nature of potential new anti-HIV lead compounds, to identify and dereplicate additional recurring classes of antiviral compounds, and to select chromatographic procedures for initial fractionation of natural product extracts. FIG. 3 illustrates the overall dereplication and chemical screening strategy.

Julian et al at Eli Lilly and Company have developed a system that delivers data with reasonable throughput (Julian, R. K. Jr.; Higgis, R. E.; Gygi, J. D.; Hilton, M. D., "A Method for Quantitatively Differentiating Crude Natural Extracts Using High-Performance Liquid Chromatography-Electrospray Mass Spectrometry", *Anal. Chem.*, 1998, 70, pp 3249–3254). The system comprises three components: (a) HPLC separation using standard reversed-phase $C_{18}$ gradient separation on the crude extract. (b) ESI-MS detection of effluent analytes, and (c) a computational image analysis techniques, the data are reduced to a list containing the m/z value and retention time of each ion. The ion lists are then compared in a pairwise fashion to compute a sample similarity index between two samples to allow effective comparison of the large data sets that are generated by the analysis.

Identifying the activity of compounds in complex mixtures, and isolating the active compounds, has been a method in the field of drug discovery for more than a century. Interestingly, many complex mixtures for use in humans contain only partially characterized complex mixtures, as found for example in herbal medicines. The chromatography of complex mixtures, particularly those mixtures which contain compounds with similar physical chemical properties, routinely generates chromatograms of co-eluting compounds. Examples include the chromatography of natural and synthetic chemical libraries using mass spectrometry to detect the compounds. Overlapping peaks is an unavoidable modern experimental problem in modern drug discovery whereby chromatography of complex mixtures is used as a chemical-source for identifying active compounds.

Methods to identify and isolate the activity of compounds comprising complex mixtures frequently will involve an initial test for activity in a crude sample preparation. If there is no activity, then there is usually no reason for further testing. However, if there is one or more activities in the crude sample preparation then the task of identifying the compounds containing the one or more activities is performed. The crude mixture may in fact be not only a natural product extract, but also pooled fractions from any chemical or biological source. The conventional methods routinely used to identify the active compounds in complex mixtures include the following steps.

Step 1) Prepare the crude sample, or aliquot of the crude sample, for chromatography.

Step 2) Load the sample on a chromatography column.

Step 3) Elute compounds in the complex mixture using a mobile phase system

Step 4) Detect compounds eluting from the column and collect fractions

Step 5) Analyze the fractions for activity, but pre-treat the samples for activity analysis if necessary (for example concentrate the sample by precipitation or lyophilization)

Step 6) Identify the compounds in the fractions containing the desired activity.

It is virtually impossible to unambiguously identify the active compound in active fractions containing more than one compound. Typically the active fraction(s) is(are) re-processed using Step 1) through Step 6) with the hope that a pure compound elutes in one fraction so that unambiguous identification of the active compound has been achieved. It is not uncommon for an investigator to utilize multiple columns to fractionate the activity of compounds in complex mixtures. The adage describing this problem is that chromatography is nothing more than 'experimental fractionation'.

Note that if there are 2 or more active fractions, the number of chromatography steps significantly increases. More than 10–20 chromatography steps can result when only the first chromatography column demonstrates activity in 2 or more fractions. Numerous activity assays, sample preparation, and analysis are routine for the 'experimental fractionation' method of profiling the activity of compounds in complex mixtures.

The present invention increases the efficiency of 'experimental fractionation' in activity profiling. In one embodiment efficiency is increased by merely performing 'experimental fractionation' of the complex mixture on 2 or more columns, but instead of analyzing fractions from each column, synchronized pooling of the fractions from each column are carried out specifically for activity testing. Synchronized sample-pooling captures the time dependent flow among columns into a common fraction. In other words, if 2 chromatography columns are used, the eluent from both columns that elutes from 0–1 minute, for example, is pooled, then 1–2 minutes, etc. until the chromatography runs are completed. The reason for synchronized sample-pooling is to generate a set of pooled chromatography fractions from multiple columns that have a compound-profile and an activity profile. Mass spectrometry is optimum for obtaining a compound-profile among the synchronized sample-pool, whereas, numerous assays can be performed to obtain the activity profile of the synchronized sample-pool. Compound profiles are typically performed, for example, by spectral analysis on the fractions before they are pooled, more typically as each fraction or portion thereof is analyzed by the detector as it is eluted from the chromatography unit and thereby providing spectral data on each compound component of each fraction. Activity profiles can be assessed on the uncombined or the combined fractions. The active compounds are indicated by comparing/correlating the compound profile of the fractions with the activity profile of the optionally synchronously pooled fractions.

One or more active compounds in the complex mixture can be identified in one experiment by comparing the compound-profile to the activity profile. Note that the goal of using multiple columns with different mobile phases is to have each compound in the complex mixture elute at a different time on each column. This causes each compound in the complex mixture to be present in multiple samples of the synchronized sample-pool. The 'set of fractions' comprising the synchronized sample-pool thus contain, each compound in the complex mixture, to be present in multiple fractions. Implementing the invention involves (1) detecting the pattern of compound-peaks, and (2) the activity-peak of each compound in the 'set of fractions' prepared by synchronized sample-pooling. Compounds eluting as a distribution from columns are referred to as compound-peaks and synchronized sample-pooling results in a distribution of the compound among a few continuous fractions. An activity-peak in the synchronized sample-pools merely indicates that a few continuous fractions contain the compound and therefore the activity. It is recognized that, theoretically, if two columns were used for the present invention, each compound in the complex mixture should elicit 2 activity-peaks, for 3 columns 3 peaks, etc.

Accordingly, the present invention is directed to a method of identifying compounds having a predetermined characteristic in a complex compound mixture. The compound mixture is using a first 'set of compound separation parameters' to at least partially separate the compounds in the mixture into a series of separation variable-dependent fractions $(Fa)_n$ wherein n is the number of fractions collected using said 'first set of separation variables'. That step is repeated using a second 'set of separation parameters' to produce a second series of separation parameter dependent fractions $(Fb)_n$ wherein n is the number of fractions collected using the second 'set of separation parameters'.

In one embodiment, each of the $q^{th}$ fractions obtained using each 'set of separation parameters', wherein q is the respective order number of the fractions obtained using each set of separation parameters, are combined to provide a set of combined qth fractions. Spectral data characteristic of the compound(s) in the combined fractions are obtained on a sample of each of the uncombined or combined fractions, and each uncombined or combined fraction is analyzed to detect the presence of a predetermined characteristic, e.g., a chemical, physical or biological characteristic, to identify those combined fractions that exhibit the characteristic. Preferably the spectral data (the compound profile) is obtained on the fractions before they are combined, for example, as they are eluted from a chromatographic column. The spectral data for each of the fractions exhibiting the predetermined characteristic are compared, typically using a computer implemented algorithm, to identify the spectral data (compound profiles) common to each of said fractions exhibiting the characteristics, and the compound or compounds indicated by the spectral data common to the combined fractions are identified. Mass-spectral data, such as that collected in electronic form by a MS detector on a separation device, is one example of the data used to identify compounds having the targeted characteristic. Any other analytical techniques capable of providing compound-unique characterizing data can be used as a substitute for mass spectral analysis in combination with the characteristic testing procedure in performance of the present invention. Such analytical techniques include, for example, ultraviolet absorption analysis, Fourier transform IR and Fourier transform nuclear magnetic resonance.

In summary, the compound mixture is subjected to at least two separation processes, each using a unique set of separation parameters, each process producing a series of separation parameter-dependent fractions. The fractions or a portion of the fractions from each separation process are combined on, e.g., a order number basis, and the combined fractions are evaluated or assayed for a predetermined property or characteristic using art-recognized assay techniques. Spectral data obtained on each combined fraction (or on the component reactions of each combined fraction) are then correlated with the assay results, and deconvoluted, preferably using an algorithm to identify the spectral data (and thus the compound(s)) common to each of the "assay positive" fractions. Alternatively, and typically with less efficiency, the fractions from each separation process are analyzed individually to produce a compound profile and activity profile for each fraction.

In one preferred aspect of the present invention the separation is carried out using a chromatographic separation methodology. One of the mechanisms associated with chromatographic processes is that of a reversible equilibrium of solutes between the mobile phases and the stationary phases. Separation occurs by differential migration, or preferential retention, of the various compounds in the stationary phase comprising the chromatographic unit. The equilibrium distribution of the different solutes between the stationary phase and the mobile phase is the basis of separation in chromatography. The magnitude of solute retention is a direct result from this equilibrium and is typically expressed by a parameter, the capacity factor, $k'=(t_r-t_o)/t_o$ where $t_o$ is the dead time and $t_r$ is the retention time of the solutes. The capacity factor is therefore a stoichiometric mass distribution equilibrium of solutes between the mobile phases and the stationary phases, and its determination allows the calculation of various physicochemical values according to pre-determined algorithms. The scope of the present invention is not restricted to equilibrium-based chromatography. Several other types of non-equilibrium based separation systems can be utilized in the present invention. For instance, size exclusion chromatography and gradients that cause compounds to convert from complete affinity ($k'$ approaches infinity) to no affinity (compound elutes from the column immediately). Mobile phase conditions that cause this include pH gradients, salt gradients, and even compound gradients whereby the compound causes the displacement of some absorbed molecules. Other examples include ion exchange chromatography or separation systems where the stationary phase contains an immobilized protein or macromolecule that exhibit known binding properties (for instance immobilized enzyme, antibody or receptor).

The separation process depends on different parameters (herein referred to as separation parameters or separation variables) including stationary phase, mobile phase composition, mobile phase flow rate gradients of such parameters, temperature, and column size among others. Typically, if the same mixture of compounds is subjected to different chromatographic separation conditions (wherein each separation being carried out using a different set of separation parameters), each set of separation parameters provides a unique chromatographic profile for the mixture. In addition, no two compounds in the mixture (provided that they are not related in any special way, like enantiomers), would be affected the same way for each chromatographic condition. In other words, a particular compound will exhibit a unique and distinct "response" (chromatographic profile or signature) under any one set of chromatographic conditions. Thus, for any one compound, a set of chromatographic profiles carried out using different sets of separation parameters constitutes a "chromatographic fingerprint" unique to this compound, and the probability for any two compounds to have the same chromatographic fingerprint decreases dramatically (to become zero) as the number of chromatographic conditions used to establish said chromatographic fingerprint increases.

The solutes in the fractions from each chromatographic separation can be analyzed by mass spectrometry (MS) or other detector capable of providing spectral data useful for providing identifying characteristics of the various compound solute. The pattern of the molecular ions detected by MS reflects the elution profiles of each compound detected for each separation and thus provides a molecular weight profile of the compounds eluting from the chromatographic unit. This is the basis of the LC/MS technology: the LC unit allows partial separation of the mixture of compounds injected onto the system (typically collected in a series of fractions), and the MS provides structural information on the compounds in each fraction.

Currently, automated, semi-quantitative assessment of combinatorial libraries is most readily accomplished by coupling HPLC with UV detection and mass spectrometry. Rapid HPLC methods with columns capable of delivering high-resolution separations have been developed in recent years, and have been well received by the drug discovery industry as a powerful tool particularly suited to handle the expanding analytical needs of combinatorial chemistry. The ability to characterize chemical libraries derived from combinatorial synthesis has in turn revealed that the purity of the compounds generated by this method is not necessarily high enough for biological evaluation of these compounds. Consequently, the scope of the high-throughput HPLC techniques initially designed and developed for structure confirmation purposes has expanded to include purity assessment and purification of the compound libraries to make them suitable for biological screening. One of the limitations of the LC/MS methods currently used in the drug discovery industry is that, unless all the compounds injected on the column are nearly perfectly resolved, bioassay evaluation of the collected fractions is usually not relevant since one or more "active" fraction may contain more than one compound. The task is then to determine which compound(s) in the fraction of interest is (are) responsible for the "positive" assay results.

In one embodiment of this invention there is provided a method of using HPLC coupled with a mass spectrometer to produce at least two sets of eluent fractions (or sets of data reflecting k' and peak widths deriving from the separation process) of a complex compound mixture, each obtained using a distinct set of chromatographic separation parameters. The data can be recorded with concomitant collection of a series of fractions (one series of fractions per set of separation variables), or the mass spectral data can be obtained on each fraction or combined fractions. Thus for the first set of separation parameters (run (a)), fractions $F_{a1}$, $F_{a2}, \ldots, F_{an}$ are collected, and the solution eluting from the chromatographic system is either simultaneously analyzed by MS, or analyzed on a fraction-by-fraction basis. Using a second unique set of separation parameters (run (b)), fractions $F_{b1}$, $F_{b2}, \ldots, F_{bm}$ are collected with concomitant determination of the chromatographic elution profile by MS detection. After the fractions for each chromatographic run are collected, all the $q^{th}$ fractions (where q is the order number of the fraction) obtained from each separation parameter-dependent chromatographic separation are combined and the respective combined fractions are assayed/analyzed for the presence of a predetermined characteristic, e.g., a physical, chemical or biological property. Optionally, but with less efficiency, the fractions can be assayed individually. Any art-recognized assay can be used to analyze the combined fractions, including antibody-, receptor-, or enzyme-based specific binding base assays, electrochemical assays, photometric/fluorescence assays, disc assays, calorimetric assays, cytotoxicity assays and the like. The fractions that exhibit the targeted property are identified and a computer pattern-matching algorithm (e.g., fraction activity vs. mass spectral data or other compound characterizing data) for the "active" fractions is used to identify the chemical entities in the initial complex compound mixture that exhibit the chemical, biological, or physical property of interest. The mass spectral data can be collected in electronic form and used as input for a computer algorithm for processing the data and correlating it with those fractions which are found to exhibit the target activity or characteristic. The mass spectral data (or spectral data from another detection device) can be collected continuously during fraction collection, they can be collected on each fraction from each run, or they can be collected on each of the respective combined fractions.

BRIEF DESCRIPTION OF THE DRAWINGS

FIG. 1 depicts the chemical screening patterns for HIV-inhibitory standards. The 3×4 matrix represents four fractions each from three different chromatography media. Heavily shaded boxes indicate elution of anti-HIV activity comparable to a control sample of the standard antiviral agent. More lightly shaded boxes indicate elution of activity of lower potency than the control; open boxes indicate no elution of anti-HIV activity.

FIG. 2 details the chemical screening patterns for sponge extracts containing sulfated sterols. The 3×4 matrix represents four fractions each from three different chromatography media. Heavily shaded boxes indicate elution of anti-HIV activity comparable to a control sample of the extract supernatant. More lightly shaded boxes indicate elution of activity of lower potency than the control; open boxes indicate no elution of anti-HIV activity.

FIG. 3 depicts the overall dereplication and chemical screening strategy used by Boyd et al.

FIG. 4 pictures four chromatographic profiles of the same mixture of six compounds on the same column, using different gradients.

FIG. 5 depicts the individual elution profiles corresponding to FIG. 4.

FIG. 6 outlines the chromatographic fingerprints of each compound (A–F) derived from their respective elution profiles (as shown on FIG. 5).

FIG. 7 outlines the iterative process of the pattern matching algorithm.

FIG. 8 depicts an example of peak order reversal with two chromatographic runs using a C18 column and a Silica column.

FIG. 9 is a representation of an eluent switch interfaced LC/MS system.

FIG. 10a describes the instrumental set up used in the multiple Enzyme Linked Immunosorbent Assay (ELISA) experiment.

FIG. 10b describes the flow gradient profile used in the multiple ELISA experiment.

FIG. 11 depicts the representative structural features that will produce a positive result in the Benzodiazepine, Haloperidol, and tricyclic ELISA tests respectively.

FIG. 12 describes the principle of Enzyme Linked ImmunoSorbent Assays (ELISA).

FIG. 13a shows the total Ion chromatograms generated from loading a complex mixture of 70 compounds on an $^{Ester}$IAM.PE$^{C10/C3}$ column. (See WO 99/10522 for a detailed description of the specified HPLC columns.)

FIG. 13b shows the total Ion chromatograms generated from loading a complex mixture of 70 compounds on an $^{Ester}$IAM.PS$^{C10/C3}$ column.

FIG. 13c depicts the results of haloperidol ELISA analysis of combined fractions from the chromatographs shown in FIGS. 13a and 13b.

FIG. 14 depicts the combination of fractions from two chromatographic runs into one single series of fractions for the ELISA assay.

FIG. 15 shows the results of the Haloperidol ELISA carried out in experimental section B.

FIG. 16 shows the resolution of Haloperidol (16A) with Chloroquine (16B) on an $^{Ester}$IAM.PE$^{C10/C3}$ column, but not on an $^{Ester}$IAM.PS$^{C10/C3}$ column.

FIG. 17 depicts the co-elution of Benzydamine (17A) with Haloperidol (17B) on an $^{Ester}$IAM.PE$^{C10/C3}$ column, but not on an $^{Ester}$IAM.PS$^{C10/C3}$ column.

FIG. 18 shows the chemical structures of the test compounds used in the multiple ELISA assay experiment (section C).

FIG. 19 depicts the elution order of Diazepam, Haloperidol, Hydroxyzine, Imipramine, Orphenadrine, Oxyphencyclimine, and Propafenone on $^{ester}$IAM.PE$^{C10/C3}$ and $^{ester}$IAM.PS$^{C10/C3}$ columns.

FIG. 20 shows the chromatographic fingerprints of Diazepam, Haloperidol, Hydroxyzine, Imipramine, Orphenadrine, Oxyphencyclimine, and Propafenone on $^{ester}$IAM.PE$^{C10/C3}$ and $^{ester}$IAM.PS$^{C10/C3}$ surfaces.

FIG. 21 depicts the results from the Benzodiazepine, Haloperidol, and tricyclic ELISA assays.

FIG. 22 shows the fingerprint match between the Benzodiazepine and Haloperidol ELISA assays and the two-separation-parameter-chromatographic profiles of Diazepam and Haloperidol respectively.

FIG. 23 shows the fingerprint match between the tricyclic ELISA assay and the two-separation-parameter-chromatographic profiles of Imipramine and Oxyphencyclimine.

FIG. 24a depicts the expected elution order of AZT, Olazoline, Norfloxacin, Nikethamide and Mescaline on an IAM.PC column.

FIG. 24b depicts the expected elution order of AZT, Olazoline, Norfloxacin, Nikethamide, and Mescaline on an IAM.PE column.

FIG. 25a pictures the expected chromatographic profile of a mixture of AZT, Olazoline, Norfloxacin, Nikethamide, and Mescaline on an IAM.PC column.

FIG. 25b depicts the expected chromatographic profile of a mixture of AZT, Olazoline, Norfloxacin, Nikethamide, and Mescaline on an IAM.PE column.

FIG. 26 depicts the chromatographic fingerprints of AZT, Olazoline, Norfloxacin, Nikethamide, and Mescaline derived from two chromatographic runs using an IAM.PC column and an IAM.PE column.

DETAILED DESCRIPTION OF THE INVENTION

The present invention is directed to a method for identifying one or more compounds having a predetermined chemical or biological property in a complex compound mixture. The method requires at least partial separation of the compound mixture using at least two different sets of separation parameters, and collection of the partially separated mixture of compounds into two distinct series of separation variable-dependent fractions (one series of fractions per set of parameters).

In one embodiment the partial separation is effected by a chromatographic unit, which can be any chromatographic system that can be interfaced with an analyzer or detector, and can include (but is not limited to) high-performance liquid chromatography (HPLC) columns, capillary electrophoresis chromatography (CEC) columns, super-critical fluid (SCF) columns and microchips. Microchips are planar glass substrate etched with a channel network. They represent the ability to miniature traditional "benchtop" separation methods with the advantages of speed, automation, and volumetric reduction of both sample and waste. The successful interfacing of microchips and mass spectrometry makes this method amenable to implementation for the purpose of the invention.

Capillary electrophoresis (CEC), a hybrid of HPLC and CE, constitutes a novel technique for the separation field. In CEC, the packed capillary column serves as the injector, pump, separation column, and detector cell. CEC has high efficiency for the separation of both neutral and charged compounds. A plug-like electroosmotic flow (EOF) enables CEC to separate neutral molecules without the use. of surfactants, and makes CEC more amenable to coupling with MS.

The detector unit is any instrument capable of producing signals/data that allow detection, quantification and/or identification of the physicochemical characteristics and/or chemical structure of compounds alone or in mixtures with other compounds. Exemplary of such detectors is a mass spectrometer (MS), a Fourier transform infra red spectrometer (FTIR), a Fourier transform ultra violet spectrometer (FTUV), standard UV detector, fluorescent detector, electrochemical detector, and a Fourier transform nuclear magnetic resonance spectrometer (FTNMR).

The success of the method presented in this invention requires selection of separation parameters for achieving distinguishable parameter-dependent profiling of a mixture of compounds. In the case where the separation is effected by a chromatographic unit such as an HPLC, one such parameter is the type of column (stationary phase) used. More specifically, parameter-dependent non-specific binding (as opposed to "specific binding") may be used as a way to differentiate two or more compounds in a test solution. Exemplary of specific binding is the affinity exhibited between a receptor molecule and a compound wherein the receptor molecule includes a defined binding locus that discriminatorily binds one or more compounds having a predetermined chemical structure. Compounds not having the predetermined chemical structure do not bind with the binding site of the receptor molecule. "Compound-dependent non-specific binding" as used herein refers to that affinity interaction between a compound and a surface that does not have a specific discriminative binding locus for that compound, but rather the binding derives from the concomitant hydrophobic and/or hydrophilic interactions between the surface and the compound. Non-specific binding between a surface and a compound is "compound-dependent" in that, for any one surface, different compounds will interact and bind with such surface to varying degrees based upon the chemical structure and hydrophobic/hydrophilic nature of the compound. The choice of the chromatographic materials (both solid phase and mobile phase) will essentially depend on the types of compounds to be analyzed, the type of application under consideration, as well as which type of surface/solute interactions are under investigation.

Various types of columns can be used to implement the proposed method, whether differing in size (analytical or preparative), solvent compatibility, stationary phase or any other characteristic relevant to use as a chromatographic unit. For example, various covalently bound stationary phases can be used as the separation surfaces: chromatographic material can be employed, whether commercially available (silica, $C_{18}$, $C_8$, $C_4$, chiral packing material, gel permeation material, ion exchange resins or other available chromatographic material) or material specifically designed and developed for a particular application or investigation. The chromatographic material may contain immobilized protein(s) or macromolecule(s) which exhibit known specific binding properties. Exemplary of such macromolecules are receptors, enzymes, or antibodies. One group of surfaces is so-called membrane mimetic surfaces. The term "membrane mimetic surface" refers to any surface bearing immobilized amphiphilic molecules (i.e., those having both lipophilic and hydrophilic portions) capable of exhibiting some affinity for or otherwise interacting with a solute (e.g., a test or control compound) in a fluid phase in contact with the surface. The term is intended to encompass a broad scope of commercially or non-commercially available stationary phases. Membrane mimetic surfaces include those described in U.S. Pat. No. 4,931,498, and in PCT International Publication WO 99/10522.

As exemplified in FIG. 4, a possible separation variable to consider is the gradient of the mobile phase (e.g. the variation of the mobile phase composition as a function of time). FIGS. 4a, 4b, 4c, and 4d picture the chromatographic profiles of a mixture of six compounds (A, B, C, D, E, and F) on identical columns (for example C18 columns) with, for instance, 20 min., 40 min., 60 min., and 80 min. solvent gradients respectively (for example acetonitrile/water mobile phase). MS analysis of the eluting solution for each chromatographic run would return the individual elution profiles of each compound as depicted on FIG. 5. Combining on the same graph the elution peaks of one given compound collected under the four different chromatographic conditions (i.e. in the example, at four different solvent gradients) establishes the chromatographic fingerprints for said compound under the selected chromatographic parameters. FIG. 6 depicts the individual chromatographic signatures of compounds A–F established from the chromatographic profiles pictured on FIG. 5. Said chromatographic fingerprints may be used as a tool to screen/evaluate the compounds for a particular property (chemical or biological). This may be achieved by fractionation of each chromatographic run into n fractions, producing four series of fractions. Thus fractions $Fa_1$, $Fa_2$, ..., $Fa_j$ will be collected for run (a). Similarly, chromatographic runs (b), (c), and (d) will result in the collection of three series of fractions: $Fb_1$–$Fb_k$, $Fc_1$–$Fc_m$, and $Fd_1$–$Fd_n$. Combining each $q^{th}$ fraction from each of the four chromatographic runs will result in a single series of fractions $F_1$ through $F_p$, wherein q is the order number of the fractions obtained from the four runs, and p is the highest number of fractions collected among all four runs. Upon evaluation of each fraction for evidence of a predetermined property, one or more fraction may be identified as exhibiting said property. Assuming that the assay or evaluation method involves a response proportional to the amount of compound present in the sample (which is generally the case), the distribution of the property in the series of combined fractions will show a unique pattern which will correspond to that of the compound(s) exhibiting said property. The pattern matching will essentially rely on three main parameters: the position of the peak (retention time), the peak width and peak intensity. For example, if the activity pattern resembles that depicted in FIG. 5, with activity detected at times 3, 9, 15, and 21 minutes, it can be concluded that the mixture of six compounds contain a component that exhibits said property, and that it is most probably compound D. A pattern-matching algorithm comparing the "property pattern" against the "chromatographic signatures" of all six compounds individually will match the targeted property with the only compound(s) in the mixture whose fingerprint, or combination of fingerprints, more closely overlaps the property pattern.

Interestingly, irreversible binding of compounds may occur on one column but not another. However, this may not be a limitation of the present invention. Consider for instance the use of 4 columns and irreversible binding of the target compound on one column. Although 4 activity peaks are expected, only 3 activity peaks will be found. If the 3 activity peaks have no overlapping compounds with identical detection, the active species will be detected in spite of the compound eliciting irreversible binding.

One algorithm that may be used in carrying out the pattern matching aspect of this invention is outlined on FIG. 7. Briefly, after two chromatographic runs (using two different sets of separation parameters), the chromatographic signatures of each compound detected are established and compared to each other. If they are determined to be distinct enough, then the series of combined collected fractions is processed for chemical/biological property evaluation and the resulting "property pattern" analyzed to determine which combination of said chromatographic fingerprints add up to form the property pattern. If further chromatographic resolution is desired to improve the uniqueness of the chromatographic fingerprints, an additional chromatographic run can be performed (using a third set of separation variables). In theory the process can be iterated as many times as is believed to be necessary to optimize segregation of the active compounds in separate combined fractions. The algorithm may be written such that it takes into account the sensitivity of the target property assay method and the shape and size of the peaks of the eluting compounds. For instance, one or more compounds in the mixture may elute as a broad and flat peak in at least one of the chromatographic runs. The particular compound(s) will therefore be distributed over several fractions, and the quantity of compound in each fraction may not be sufficient to be detected by the chemical/biological assay. This could result in a "property positive" pattern which could complicate the screening procedure. A possible solution to circumvent this obstacle would be to set a threshold to indicate that compounds whose m/z signal does not exceed a certain limit can most likely not be detected by the assay in use, and therefore will not show up in the final property pattern. A typical HPLC-MS instrument will output data comprised of mass spectra at sequential time intervals. Mass spectra are typically output as two-dimensional arrays of ion intensity signal as a function of mass. Software routines are used for determination of which mass ranges correspond to a single compound. Extracting this mass range as a function of time creates the chromatogram of a single compound on a given chromatographic surface. Once single compound chromatograms are determined, the software adds them to obtain mixture chromatograms corresponding to sums of single compound responses on the same chromatographic surfaces as the fraction-resolved activity determination.

For the activity profile, the software will interpret the instrument signal (whether it is a voltage, transmittance, absorbance) and convert it to a useful quantity that is associated with activity. A threshold value may be associated with a desired level of activity, and a profile of which fractions meet the criterion may be generated. The activity profile of a given collection of fractions is then stored for comparison to the corresponding combined-chromatographic data.

For the purpose of the present invention, it is not necessary that additional chromatographic runs be carried out until the chromatographic fingerprints for each of the compounds detected are strictly unique. The pooled fractions may be assayed after a pre-determined number of chromatographic runs have been performed. The activity profile will show the chromatographic region(s) where the activity of interest elutes, and will indicate for which compounds (eluting within the area where the activity elutes) a chromatographic fingerprint should be established for comparison with the activity profile, and subsequent identification of the active compound(s) in the mixture. An example of application of this strategy is described in the experimental section.

An additional possible separation variable to consider is the delivery rate of the mobile phase through the chromatographic system (e.g. the variation of the flow rate of the mobile phase as a function of time). The separation of multi-component samples by LC under fixed experimental conditions (i.e., normal elution) is often complicated by large differences in the relative migration rates of the various components. This leads to poor separation of the first eluted compounds and/or excessive separation times in addition to difficult detection for the last eluted compounds. The need for shorter analysis time and reduced peak width (resulting in a decrease in minimum detectable quantity) prompted the development of gradient chromatography. At present, there are four possible techniques of achieving gradient formation in liquid chromatography: solvent programming, stationary phase programming (coupled columns), temperature programming, and flow programming. Each of these various techniques is based on a selective change in band migration rates during separation, such that strongly retained bands are made to elute more rapidly than would be the case in normal elution. Therefore, each of these techniques could be utilized as a separation parameter for the purpose of the present invention.

Stationary phase programming could also find use with the present invention in that coupling two or more columns, which exhibit different binding properties, will result in chromatographic profiles characteristic of the selected set of chromatographic parameters. These parameters include the type of stationary phase, and the order in which they are incorporated into the chromatographic system; as well as the mobile phase gradient (variation of mobile phase composition as a function of time) used. For instance, one chromatographic column may be one with a specific immobilized receptor, and a second chromatographic unit may be a C18 column. Elution of a compound mixture on this system will result in the immobilization of those compounds in the mixture that have affinity for the receptor, while the rest of the compounds in the mixture will elute through the C18 column and will be characterized by the detector. When the mobile phase composition is switched to one that produces the release of those bound compounds from the receptor sites, they will elute through the C18 column and ultimately be identified by the detector.

An important aspect for optimum utilization of the present invention is to identify sets of separation parameters that produce significantly different chromatographic responses among all compounds. For example, this can be achieved by using chromatographic surfaces that address different chemical properties (such as polarity, charge, molecular size, and weight), and potentially effect distinctive retention differences of the eluting solutes. For example, two chromatographic runs of a mixture of compounds on a C18 column (non-polar surface) and a silica column (polar surface) respectively (FIG. 8), would result in two chromatograms where the sequence of the compounds eluting from the columns (peaks) would essentially be reversed (e.g. on the C18 column the more polar solutes would come out first, while they would elute last on the silica surface). This would maximize the chances to obtain unique and distinct chromatographic fingerprints for each compound detected, and would reduce the risk of error or erroneous assignment by the pattern matching algorithm. For any one compound, the dispersion of the retention times (recorded for each distinctive-separation parameter chromatographic run) would be maximum and the resulting chromatographic fingerprint better suited for optimum pattern matching. This is particularly important when repetitive experiments on the same sample need to be performed, for example for the QC of a mixture.

Evidence to support the mobility difference of molecules on different supports can be found in the literature. For example, Horst et al developed an assay system for the identification of retinoid compounds in biological fluids. [Horst, R. L; Reinhardt, T. A.; Goff, J. P.; Nonnecke, B. J.; Gambhir, V. K.; Fiorella, P. D.; and Napoli, J. L. Identification of 9-cis,13-cis Retinoic Acid as a Major Circulating Retinoid in Plasma., *Biochemistry*, 1995, 34, pp 1203–1209]. In this work it was necessary to quantitate the amount of different retinoic acid isomers. After sample extraction and methylation with diazomethane, the researchers found that there was a difference in the mobility of the compounds on different phases. On silica gel (normal phase), the test samples eluted as follows: 13-cis-MeRA (10.5 min), 9-cis-MeRA (11 min), 9-cis,13-cis-MeRA (11.5 min) and all trans-MeRA (13 min). The same sample was analyzed using reverse phase HPLC (RP-HPLC), which resulted in a different elution order. The elution order was changed to: 13-cis-MeRA (17 min), 9-cis,13-cis-meRA (18 min), 9-cis-MeRA (21 min), and all trans-MeRA (23 min). Similar results could be seen with comparing the free acids (normal vs. RP-HPLC).

VanRollins and Murphy found that hydroxydocosahexanoates, synthesized under autooxidation conditions, also had different chromatographic behaviors on these two systems. In their work [VanRollins, Mike and Murphy, Robert C. Autoxidation of Docosahexaenoic Acid: Analysis of Ten Isomers of Hydroxydocosahexaenoate. *J. Lip. Res.*, 1984, 25, pp 507–517.], the researchers subjected commercially available docosahexaenoic acid to autooxidation by exposure to molecular oxidation and then reduction of the hydroperoxide with sodium borohydride. This process gave a mixture of monoalcohols, hydroxydocosahexanoates. Esterification with diazomethane and chromatographic analysis illustrated a difference in the mobility on the two phases. Using a reverse phase column, the elution order was 20-, 16-, 17, 13-, 14-, 10-, 11-, 7-, 8-, and then 4-hydroxydocosahexanoate. With normal phase chromatography, the order of elution was 17-, 14-, 16-, 13-, 11-, 20-, 10-, 7-, 4-, and then 8-hydroxydocosahexanoate.

Similarly, changing the composition of the mobile phase (in particular the pH: acidic versus basic, or ascending versus descending pH gradient) may achieve similar distinctive retention differences depending on the chemical nature of the compounds to screen.

One implementation strategy for optimum utilization of the present invention is to a high throughput multi-column LC/MS system such as one described in U.S. patent application Ser. No. 09/499,904, filed Feb. 8, 2000. Briefly, a set of two or more chromatographic columns individually connected to separate pumping systems (maintaining a constant flow rate through the columns) are coupled to a mass spectrometer via an intermediate eluent switch (FIG. 9). The eluent switch is a valve-containing device capable of delivering small portions of the eluent from the individual chromatographic units to the detector, typically in a sequential order. This design permits the simultaneous determination of the HPLC profiles (including structural identification) of a mixture of multiple compounds eluting from several independent chromatographic units operated in parallel. Portions of the eluent from each column are sequentially delivered to the mass spectrometer via the eluent switch which can be configured so that the "waste" (i.e. that portion not delivered to the detector) is collected in a fraction collector common to every column. The MS detector determines the presence of the compounds and delivers a signal from which the elution profile of each respective column is determined. Evaluation of each fraction against a targeted property and pattern matching of the "property profile" against the elution profile of each compound detected will identify the compounds exhibiting said property. The high sensitivity of the MS detector allows the instantaneous identification of mixtures of compounds. A mixture of 100 or more compounds can be injected simultaneously on several columns run in parallel and detected as they elute from the chromatographic system. In theory, depending on the loading capacity of the columns, a mixture of thousands of compounds can be analyzed simultaneously and in parallel on several chromatographic surfaces. The data from the MS analysis can be correlated to that of the UV detectors connected to each column, resulting in the assignment of a retention time and capacity factor for at least a portion of the injected compounds. The data can be collected electronically and used as input for the calculation of one or more physicochemical values according to predetermined algorithms or equations, and for the determination of a chromatographic fingerprint for each compound detected.

Alternatively the method presented in this invention may be implemented using a high throughput multi-column LC/MS system such as one developed by Micromass© (Manchester, UK): a multiplexed electrospray interface that is capable of sampling four individual liquid streams in rapid succession. The system comprises a single pump delivering solvent to all four columns run in parallel. The system has been integrated with the Z-Spray ion source of the Micromass© LCT orthogonal acceleration time-of-flight mass spectrometer. The inner source housing contains an array of four pneumatically assisted electrospray probe tips that are directed at the sampling cone. A hollow cylinder is positioned co-axially with the sampling cone. Two diametrically opposed circular apertures in the wall of the cylinder allow the spray from one electrospray probe tip to pass through the cylinder across the sampling cone, while all the other sprays are excluded. The spray from each probe tip is admitted in turn to the sampling cone as the cylinder is rotated by a programmable stepper motor. The source is supplied with a heated stream of dry nitrogen that facilitates the desolvation of ions in the selected stream. To monitor the four separate electrosprays, the rotor is rotated from position to position. An optical encoder indicates which spray channel is being sampled at any one time, and the data from that channel is written to its own specific data file. The system has recently been upgraded to include a total of 8 channels. One of the disadvantages of this system is that is uses a single solvent delivery system for all the columns. Thus, the user is restricted to use column of identical size and packing material if the mobile phase flow is to be split equally through each column. In addition, the system utilizes a proprietary dual orthogonal "Z" sampling technique, which cannot be readily adapted to other mass spectrometers, much less to other types of detectors. Nevertheless the instrument is of significant value since it may be modified/configured to accept multiple solvent delivery systems (one per channel) and/or a fraction collection device. It therefore gives the possibility of collecting multiple-parameter chromatographic fingerprints (up to 8 separation parameters, since the instrument has 8 channels) in the time it takes to perform a single chromatographic run.

For purposes of the present invention, it is not necessary that the individual chromatographic profiles be collected on different channels/files by the detector (as in the case of the eluent switch system and Micromass© instrument). For instance, a multi-column LC/MS system may be configured so that the eluent from each column is simultaneously introduced into the inlet of the mass spectrometer. This will result in the collection of a single chromatographic profile, which is essentially the superimposition of the individual chromatographic profiles from each channel (column). From this single profile, individual compound chromatographic fingerprints may be extracted. However this modified set up does not allow the correlation of the compounds' chromatographic behavior as a function of the specific chromatographic conditions used for each channel. In other words, the information pertaining to the interactions between the compounds and the stationary phase is lost: it cannot be determined from the final chromatographic fingerprint of a compound which peak resulted from which column. Therefore this method may not be particularly useful for mixtures of unknown compounds, for which the chromatographic behavior on each of the columns has to be determined. However, it may find applications in cases where a specific chromatographic fingerprint (e.g., the superimposition of the individual compounds chromatographic profiles from each channel) is known, expected or screened for. For example it may be of some importance for QC procedures. A multi-channel LC/MS (configured so that the eluent from each channel is simultaneously analyzed by the MS) may be set up so that the resulting chromatographic fingerprints of the test compounds will be characteristic of a predetermined property and/or set of properties. These properties may be chemical, physicochemical, biochemical or biological. Compounds may be screened for a pre-determined chromatographic fingerprint (for QC purposes for example): depending on the application, compounds with chromatographic fingerprints that match, or differ from the pre-determined profile, are flagged.

One concept demonstrating the experimental value of the present invention resides in the resolution, or lack of it, when comparing the activity profile of a complex mixture to a chromatogram compound-peak obtained by mass spectrometry. If a compound's chromatography peak exactly matches the activity peak from a single column run, then the compound eliciting activity can be determined in a complex mixture from a single run. The peak width of the activity profile routinely differs from the compound profile, which makes it virtually impossible to clearly identify the active compound. Briefly, comparing the compound distribution eluting from the column to the activity profile in fractions eluting from the column requires that peak distributions be identical from a column if only one column will be used to identify the compound. For the purpose of the present invention, this problem of comparing peaks is referred to as the resolution problem. The present invention circumvents this resolution-problem.

The present invention is generally directed to a method using any separation device (for example, but not limited to, HPLC, CEC, and microchips) that can be interfaced with a detector (MS, FTIR, FTUV, FTNMR) for the high throughput evaluation of large pools of compounds against a targeted chemical or biological property. One feature of the present invention is that it provides a general method that, in addition to providing a new edge to high throughput bioassay screening, makes full (or better) use of the detector interfaced with the chromatographic system. Since the currently used detection techniques are usually quite expensive, the commercial advantage of the invention becomes evident: if the analytical potential of the detector and the scope of its applications are increased, through the implementation of the proposed method, it becomes more cost-efficient and is therefore worth a lot more valuable to the research/industrial fields where it has numerous applications.

Applications

The present invention can be applied to the rapid and efficient collection of databases of chromatographic fingerprints for large compound libraries. Consequently it seems perfectly suited for lead identification and optimization of chemical libraries, which is a very important aspect of the drug discovery process, as well as QSAR studies. Once a "hit" compound has been identified, derivatization by the usual combinatorial chemistry tools to a large number of structurally similar parent molecules is possible. The present invention provides a convenient and efficient method for the analysis and evaluation of this pool of derivatives and the identification of one or more compounds with a data set of retention times or capacity factors (derived from the chromatographic system) that would classify the compounds of interest as potential promising new leads.

One important field of use is the broad area of natural product libraries. Searching for new pharmacologically active compounds obtained by screening natural sources has led to the discovery of many clinically useful drugs that play an important role in the treatment of human diseases. Historically, the majority of the natural product-based drugs were first discovered by traditional cell-based in vitro assays before their real molecular biological targets were identified. Today, with the progress of newer molecular biology tools and genomics research for developing bioassays, more sophisticated biological assays in addition to cell-based assays are being employed routinely in the drug discovery paradigm. The technique described in the present invention may be used for separation method development of natural product extracts (or other complex compound mixtures). The assay of a single series of fractions generated from multiple chromatographic runs using a different set of separation parameters each time, will give insight as to where the biologically interesting compounds elute in each chromatographic run (this results from the comparison of the activity profile with the chromatographic fingerprints). Consequently, the technique allows to observe how the "biological activity elution" varies with different separation parameters. This information may be useful for developing a separation scheme to isolate or purify the compound(s) exhibiting the biological activity of interest in the mixture.

In recent years a notable number of natural product-derived compounds has been discovered by employing mechanism-based screening approaches involving cellular or biochemical targets in their assay design. The importance of natural product-based drug development in the past 10–15 years is exemplified by the numerous therapeutically useful compounds (derived from natural sources) that are either in current clinical use or in various stages of clinical trial. Natural product-derived drugs find use in multiple therapeutic areas including infectious, neurological, cardiovascular, metabolic, immunological, inflammatory, and oncological diseases.

1) Infectious Diseases

The increasing clinical importance of drug-resistant bacterial pathogens has lent additional urgency to antibacterial research. Important developments of antibacterial compounds over recent years have been related to some well-known natural product classes such as b-lactams (e.g., cephalosporins), tetracyclines (e.g., glycylcyclines), macrolides (e.g, erythromycin and rifamycin analogues), spectinomycines, and glycopeptides (e.g., vancomycin and teicoplanin analogues). In the antifungal area, several known natural product classes such as polyenes (e.g., amphotericin B and nystatin analogues) and nucleosides (e.g., nikkomycin Z) have been studied.

2) Neurological Diseases

The dramatic effects of ergot (*Claviceps prupurea*) and its constituent indole alkaloids have been recognized as partial agonists or antagonists at a-adrenergic, serotoninergic, and doparninergic receptors for some times. The analogues of ergot have been in the clinical application for the treatment of migraine, Parkinson's disease, and postpartum hemorrhage. New generation of ergot alkaloid analogues is cabergoline, a potent, selective, and long-lasting dopamine D2 receptor agonist.

3) Cardiovascular and Metabolic Diseases

The discovery of natural product Mevastatin (Compactin) with the inhibitory activity against the HMG-CoA reductase was the first of a novel class of compounds now known as statins used for the treatment of hyperlipoproteinemia. Compactin was isolated from a culture of Penicillium sp., and can be converted into more active Pravastatin. Some natural products, such as squalestatins or zaragozic acid, isolated from fungal metabolites showed inhibition against squalene synthase (SQS) (enzyme involved in the conversion of farnesyl pyrophosphate (FPP) to squalene in the cholesterol biosynthetic cascade), which is considered potentially advantageous over HMG-CoA reductase inhibitions, since it does not affect the biosyntheses of other isoprenoids essential for cell growth. In addition to inhibiting cholesterol biosynthesis, natural and synthetic saponins reduce dietary cholesterol intake by decreasing absorption at the intestinal wall resulting in the reduction of plasma cholesterol levels in experimental animals, therefore they can be of potential pharmacological benefit in the treatment of hypercholesterolemia.

In the antidiabetes area, several a-glucosidase inhibitors such as Acarbose, derived from natural product sources, have been introduced. By inhibiting a-glucosidase, Acarbose decrease the release of glucose from ingested carbohydrates and slows the increase of food-induced blood glucose levels.

4) Immunological, Inflammatory, and Related Diseases

Natural products have become a rich source of immunosuppressive agents for organ transplantation. For example, since the introduction of Cyclosporine A (Sandimmune), many nonpeptide drugs have been brought into various stages of preclinical and clinical development.

Triptolide is a major active component isolated from the plant *Tripterygium wilfordii*, a plant traditionally used for treatment of rheumatoid arthritis. A variety of formulations, including capsules, topical liquids, and patches of the plant extract, were developed and are also shown to be effective in the treatment of patients with inflammatory and autoimmune disease.

5) Oncological Diseases

The discovery of active compounds against human cancers has been largely dependent upon the screening of natural products and their synthetic analogues in experimental tumors. Traditionally, natural products have been invaluable as compounds to regulate the cell-cycle, leading to fruitful achievements in the anti-tumor area in particular. Recent drug development efforts have led to either improved versions of already known active compounds or produced new generations of anti-tumor compounds, such as the vinca alkaloids (e.g., vinorelbine), anthracyclines, mitomycin analogues (e.g., KW-2149, and BMS-181174), bleomycin analogues (e.g., liblomycin), and others.

Other examples of applications are drug analysis/screening: evaluation of compounds put in contact with a surface suitable for pharmacokinetics and pharmacodynamics studies. The invention may also find applications in the field of diagnostics: physiological fluids sampling (such as blood or urine) for specific compounds that may be diagnostic of some disease or condition, or for metabolic studies, may be performed. Enzyme Linked Immunosorbent Assay (ELISA) is the most widely used diagnostic system in medical and veterinary science. The technique is highly suitable for processing large numbers of samples because it is quick and relatively low cost. The key reagents in ELISA are antibodies, which are soluble proteins produced by the immune system in response to infection by a foreign substance (an antigen). ELISA tests are used to diagnose a wide variety of diseases by identifying the disease agent itself and/or the antibodies produced against the agent. The reagents in ELISA are used in very small quantities, so mass-producing the test for use in travel kits is inexpensive. The ELISA technology has the additional benefit of being adaptable for diagnosis for almost every animal disease. Throughout the world, ELISA tests are used for diagnosis and surveillance of many livestock diseases.

The present invention may also be relevant to environmental sampling (water, soil analyses for contamination) and toxicity assessment of chemical substances. In order to control production and marketing of chemicals with potential risks, the industrialized nations have tightened up and enforced the laws regulating marketing and use of new and existing chemicals. Toxicity information for aquatic, terrestrial and wildlife populations, and information on the fate of the material is necessary in order to assess potential environment impact. Typically a battery of toxicity assays is conducted for each chemical, representing both aquatic and terrestrial organisms, and also different levels of biological organization. Many water-quality surveys have used ELISA for the analysis of the major crop herbicides in the United States (e.g., Alachlor, Atrazine, Cyanazine, Metolachlor). Most of these surveys used ELISA both as a quantitative tool and as a screening method to reduce sample load for conventional analysis. Because ELISAs can be used to screen large sample sets at realistic costs, they can facilitate large-scale surveys and monitoring programs that would otherwise be unrealistic. Herbicides can be bound to larger molecules, making them big enough to produce antibody production in animals.

The scope of applications of the invention is not limited to small molecule libraries. The method is applicable to the characterization/evaluation of large biomolecules. These biomolecules could include proteins, antibodies and oligonucleic acids and enzymatic digests thereof. One example is in the area of protein isolation and purification. The purification of membrane proteins remains an arduous task in the field of separation science. No general methods exist for purifying membrane proteins. Part of the difficulty with membrane protein purification is to identify efficient stationary phase/mobile phase combinations, particularly because many proteins require detergents in the mobile phase to maintain both functional activity and solubility of the desired membrane protein. Maintaining protein solubility is necessary to prevent protein aggregation, which is a common problem during the purification of membrane proteins. One of the most prominent problems with protein purification is identifying the target protein among contaminating proteins (non-target proteins). Regardless of the type of stationary phase that is used for the separation, the number of overlapping proteins contaminating the target protein is significant. When trying to isolate a new protein with a specific activity, the process of identifying which is the protein responsible for the activity is a difficult and time-consuming challenge.

The present invention using MS detection [for example, Matrix Assisted Laser DesorptionIIonization (MALDI) or Time of Flight (TOF) spectroscopy] will allow anyone to identify any target protein immediately even though it will be contaminated with many other proteins. This will make subsequent purification steps easier to design because the new target protein of interest can be "chemically" tracked instead of relying solely on "activity" tracking of the protein under the conditions whereby the target protein is contaminated with non-target proteins.

Another example is in the area of antibody discovery. While trying to isolate catalytic antibodies for cocaine with esterase activity, Landry et al (Yang G., Chun J., Arakawa-Uramoto H., Wang X., Gawiniwicz A., Zhao K., Landry D. W., "Anti-Cocaine Catalytic Antibodies: A Synthetic Approach to Improved Antibody Diversity", *J. Am. Chem. Soc.*, 1996, 118, pp 5881–5890) found it was necessary to perform multiple chromatographic separations in order to separate and purify antibodies from the supernatant of hybridoma cell. These separations required affinity chromatography, anion exchange HPLC, and analytical DEAD columns with different gradients for isolation. From their work, nine antibodies with some catalytic activity were discovered from a pool of 107 antianalog antibodies generated. With our method, the 107 antibodies could have been subjected to our profiling method to determine which protein was catalytically active. Then, one would have a fingerprint on obtaining the active protein in the original sample. This change would have greatly simplified the identification of single, desired catalytic antibody out of the 107 that were generated.

Another area where the current invention would be beneficial is with the discovery of antibiotics. Discovering antibiotics is often an involving process that takes advantage of clever use of chromatographic separations and solvent partitioning to separate and locate metabolites with the potential for the development as new drugs. This process could be straight forward or tedious, and often results in the re-isolation of known, bioactive molecules. To overcome this laterproblem, the present invention could be used to locate bioactive metabolites, even in complex samples, without extensive labor and cost. For example, a recent article (Holler, U., Konig, G. M., and Wright, A. D., Three New Metabolites from Marine-Derived Fungi of the Genera Coniothrium and Microsphaeropsis,. *J. Nat. Prod.*, 1999, 62, pp 114–118) suggests this need. The researchers focused on the Coniothrium and Microsphaeropsis fungi species. Initially, the crude material obtained from tissue homogenation appeared promising. They then followed a fairly standard bioassay directed fractionation procedure involving the extraction of the homogenates with ethyl acetate, chromatography on silica gel, and then repeated HPLC to purify the mixture of components. Of these isolate compounds, the presence of a large amount of mellein and hydroxymelleins (see below), compounds of known biological activity, overwhelmed the bioassay process. In the end, only three compounds of moderate biological activity were isolated. The potency of the initial extracts was attributed to the presence of the known compounds.

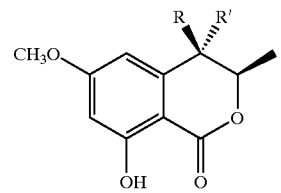

R=R'=H=mellein
R=OH=hydroxymellein

The embodiments of the invention listed above are not intended as an exclusive list of the embodiments within the scope of the present invention. It is intended that the invention not be limited by virtue of the recitation of the previous embodiments, but instead that these embodiments be considered but illustrative of the scope of the invention. Variations of such embodiments and their equivalents will be readily apparent to those of ordinary skill in the art.

Summary of Preliminary Experimental Results

The experimental design used to demonstrate the implementation of the present invention used known membrane binding constants of drugs, which were measured on chromatographic surfaces that mimic membranes. The preferred, if not only surfaces capable of measuring membrane binding constants so far are from a group of immobilized artificial membranes (IAMs). IAMs consist of a monolayer of phospholipids covalently immobilized to a silica surface. Five types of IAM surfaces are typically used: phosphatidylcholine (PC), phosphatidylethanolamine (PE), phosphatidylserine (PS), sphingomyelin (SM), and cholesterol (CL).

These IAM silica surfaces are used as the stationary phase in high performance liquid chromatography (HPLC). The IAM columns can be run in parallel with one single MS detection system (multi-column LC/MS) or successively using a one-column LC/MS instrument.

A. General Experimental Procedures

I. LC/MS Conditions

The present experimental design utilized the one-column-one-LC/MS set up shown on FIG. 10a. The LC/MS system comprised a Hewlett Packard HPLC (HP 1100 series) interfaced with a Bruker Esquire-MS spectrometer. The HPLC had two binary pumps and a Diode Array Detector (DAD). The mobile phase was a 0.01M PBS solution with 15% acetonitrile and the pump system was programmed to deliver a step flow gradient ranging from 0.5 to 4 mL/min. The flow gradient profile is described on FIG. 10b.

II. Phosphate Buffer Solution

The Phosphate Buffer Saline (PBS) solution was prepared by dissolving 0.2 g of potassium phosphate monobasic, 1.15 g of sodium phosphate dibasic, and 2.922 g of sodium chloride in 1 L of deionized water. This produced a PBS buffer with a 0.01M phosphate, 0.067M salt, and pH around 7.5.

III. Chromatographic Columns

The data for this experiment was collected on 4.6×30 mm $^{ester}$IAM.PE$^{C10/C3}$ and 4.6×30 mm $^{ester}$IAM.PS$^{C10/C3}$ columns. (See PCT/US98/17398 published as International Publication WO 99/10522 for a detailed description of the identified HPLC columns.)

IV. ELISA Test Kits

ELISA test kits were purchased from Neogen Corporation, Lexington, Ky. Three ELISAs were used: Benzodiazepines (test specific for compounds belonging to the Benzodiazepine family, such as Alprazolam, Clobazam, Diazepam, Temazepam, . . . ), Haloperidol (specific for Haloperidol), and tricyclics (specific for a group of compounds with tricyclic structure. Examples of compounds belonging to this group are Amitriptyline, Doxepin, Cyclobenzaprine, Nortriptyline, Clomipramine, Imipramine, and Trimipramine). Structural features that typically produce a positive response for each of these assays are described on FIG. 11.

ELISA is a method of analysis that relies on specific interactions between antibodies and antigens to detect a variety of substances. The assay (Neogen) operates on the basis of competition between the horseradish peroxidase (HRP) enzyme conjugate and the analyte in the sample for specific binding sites on the precoated antibody microplate. The test kits used for the experiment are 96-well plates precoated with a specific antibody. As described in FIG. 12, the sample or standard solution is first added to the precoated antibody microplate. Next, the diluted enzyme conjugate is added and the mixture is shaken and then incubated at room temperature for one hour. During incubation, competition for binding sites on the microplate is taking place. The plate is then washed removing all unbound material. The bound enzyme conjugate is detected by the addition of a tetramethylbenzidine (TMB) based substrate which generates an optimal color after 30 minutes. Quantitative test results may be obtained by measuring and comparing the absorbance reading of the wells of the samples against the standards with a microplate reader at 650 nm. The extent of color development is inversely proportional to the amount of analyte in the sample or standard. For example, the absence of the analyte in the sample will result in a bright blue color, whereas the presence of the analyte will result in a light blue color or no color as the concentration of the analyte increases. Typically, the sensitivity of the selected ELISA assays ranges from ~0.1 to 20–30 ng/mL depending on the substrate.

V. Microplate Reader

The absorbance for each well of the ELISA microplates was determined with a Multiskan RC model 5111 320 from Labsystems.

B. Single ELISA Experiment

The objective of this experiment was to demonstrate that the present invention allows to identify an active compound (or a group of active compounds) in a complex mixture of more than 50 compounds. The sample mixture contained 70 drugs (including haloperidol), which are listed in Table 1. The sample mixture was run on two IAM columns ($^{ester}$IAM.PE$^{C10/C3}$, and $^{ester}$IAM.PS$^{C10/C3}$) which generally produce significantly different band migration rates during separation. Fractions were collected and pooled according to the method described in the present invention (FIG. 14). The combined fractions were assayed for Haloperidol using ELISA.

TABLE 1

| Item | Compound Name | m/z | IAM.PE tr (min) | IAM.PS tr (min) |
|---|---|---|---|---|
| 1 | acebutolol | 337 | 3.59 | 17.03 |
| 2 | adiphenine | 312 | 22.66 | 53.91 |
| 3 | alprenolol | 250 | 14.48 | 44.94 |
| 4 | amsacrine | 394 | 30.9 | 39.96 |
| 5 | antazoline | 266 | 14.56 | 36.18 |
| 6 | atropine | 290 | 3.77 | 16.81 |
| 7 | benoxinate | 309 | 18.52 | 38.25 |
| 8 | benzetimide | 363 | na | na |
| 9 | benzydamine | 310 | 26.73 | 89.11 |
| 10 | berberine | 336 | 12.53 | 29.28 |
| 11 | brompheniramine | 321 | 20.12 | 48.52 |
| 12 | camylofin | 321 | na | 56.92 |
| 13 | carbetapentane | 334 | 20.24 | 56.42 |
| 14 | chlordiazepoxide | 322 | na | na |
| 15 | chloropyramine | 290 | 23.8 | 72.91 |
| 16 | chloroquine | 320 | 16.61 | 88.8 |
| 17 | chlorpheniramine | 275 | 17.42 | 40.59 |
| 18 | clenbuterol | 277 | 6.65 | 24 |
| 19 | clopamide | 368 | 3.96 | 3.66 |
| 20 | cyclizine | 267 | 22.43 | 53.64 |
| 21 | cyclopentolate | 292 | 12.23 | 25.46 |
| 22 | dexetimide | 363 | 19.14 | 36.22 |
| 23 | diazepam | 285 | 20.73 | 21.34 |
| 24 | diltiazem | 415 | 24.83 | 50.09 |
| 25 | diphenhydramine | 256 | 16.77 | na |
| 26 | dobutamine | 302 | na | na |
| 27 | doxepin | 280 | 24.86 | na |
| 28 | dyclonine | 290 | na | na |
| 29 | ephedrine | 148 | 2.07 | 13.5 |
| 30 | ethaverine | 396 | 46.04 | 49.02 |
| 31 | fenoterol | 304 | 3.88 | 17.6 |
| 32 | fenspiride | 261 | 5.76 | 13.84 |
| 33 | flecainide | 415 | 15.01 | 41.86 |
| 34 | flurazepam | 388 | 21.1 | 41.36 |
| 35 | glafenine | 373 | 38.19 | 40.94 |
| 36 | guanabenz acetate | 231 | 16.39 | na |
| 37 | haloperidol | 376 | 26.2 | 92.58 |
| 38 | hydroxyzine | 375 | 30.64 | na |
| 39 | imipramine | 281 | na | na |
| 40 | ipratropium | 332 | 2.29 | 11.02 |
| 41 | ketoconazole | 531 | na | na |
| 42 | labetalol | 329 | 13.41 | 40.59 |
| 43 | loxapine | 328 | 42.36 | 87.22 |
| 44 | medazepam | 271 | 40.5 | 40.44 |
| 45 | methapyrilene | 262 | 12.04 | 27.2 |
| 46 | methoxyphenamine | 180 | 3.49 | 18.01 |
| 47 | mianserin | 265 | 41.01 | 87.49 |
| 48 | mifepristone | 430 | na | na |
| 49 | naftopidil | 393 | 58.06 | 109.44 |
| 50 | orphenadrine | 181 | 21.45 | 61.56 |
| 51 | oxybutynin | 358 | 59.76 | 121.38 |

TABLE 1-continued

| Item | Compound Name | m/z | IAM.PE tr (min) | IAM.PS tr (min) |
|---|---|---|---|---|
| 52 | oxymetazoline | 261 | 15.4 | 39.16 |
| 53 | oxyphencyclimine | 345 | 20.42 | 60.48 |
| 54 | oxyphenonium | 348 | 15.22 | 37.64 |
| 55 | phenyltoloxamine | 256 | 27.12 | na |
| 56 | prazepam | 325 | 33.88 | 34.57 |
| 57 | procyclidine | 288 | 22.13 | 73.72 |
| 58 | propafenone | 342 | na | na |
| 59 | propantheline | 368 | 18.83 | 47.48 |
| 60 | quinine | 325 | 17.92 | 48.37 |
| 61 | salbutamol | 240 | 1.24 | 5.77 |
| 62 | terfenadine | 472 | na | na |
| 63 | thiazesim | 327 | 22.77 | 47.91 |
| 64 | timolol | 317 | 3.34 | 18.55 |
| 65 | tolazoline | 161 | 1.73 | 8.9 |
| 66 | tracazolate | 305 | 43.78 | 44.55 |
| 67 | trihexyphenidyl | 302 | 24.26 | 81.9 |
| 68 | tropicamide | 307 | 4.71 | 5.01 |
| 69 | tropine3,5dichlorobenzoate | 314 | 28.4 | na |
| 70 | zolpidem | 308 | 15.11 | 15.67 |

The sample solution (0.6 µg/µL total concentration in 0.01M PBS buffer containing 30% DMSO) containing the 70 test compounds (~0.0086 µg/µL per compound) was injected (sample loop 20 µL) on an $^{ester}$IAM.PE$^{C10/C3}$ column. The mobile phase was delivered into the LC according to the flow gradient profile described on FIG. 10b. Fractions were collected at 1.5 min intervals. The chromatographic run was stopped after 80 minutes (52 fractions), when the last detectable compound (Oxybutynin) eluted from the column. The chromatographic profile is depicted on FIG. 13a, showing substantial overlap between the compounds. The sample mixture was then run on an $^{ester}$IAM.PS$^{C10/C3}$ column using the same conditions described above. Fractions were collected every 1.5 minutes. The chromatographic run was stopped after 147 minutes (96 fractions), when the last detectable compound (Oxybutynin) eluted from the column. The chromatographic profile is shown on FIG. 13b.

The retention times of each detected compound on $^{ester}$IAM.PE$^{C10/C3}$ and $^{ester}$IAM.PS$^{C10/C3}$ are listed in Table 1. Note that 10 compounds were not detected during the IAM.PE run, and that 15 compounds were not detectable during the IAM.PS run, due to low signal intensity.

The series of 96 fractions for the ELISA assay was created by taking and combining aliquots (150 µL) from the fractions collected for each chromatographic run as described in FIG. 14. For clarity purposes, the fractions generated for the ELISA assay will be denoted $^{Assay}$fractions to distinguish them from the fractions collected from the chromatographic runs. Note that $^{Assay}$fractions 53 through 96 were generated by mixing an aliquot (150 µL) of each fraction from the IAM.PS chromatographic run with an equal volume of 15% acetonitrile/PBS buffer. This is to compensate for the fact that the IAM.PE run was significantly shorter than the IAM.PS run, and only generated a total of 52 fractions (as opposed to 96 fractions for the IAM.PS run). Consequently fractions 53–96 were diluted with mobile phase to ensure a consistent concentration in compounds across the series of 96 $^{Assay}$fractions. Each $^{Assay}$fraction was diluted 10 fold to account for the high sensitivity of the Haloperidol ELISA (0.06 ng/mL), and to avoid saturation of the assay.

The ELISA tests were conducted as follows. 20 µL of each sample solution (96 $^{Assay}$fractions) was added into an ELISA well (one well per $^{Assay}$fraction) of a 96-well plate. 180 µL of diluted enzyme conjugate solution (1 µL of Neogen's enzyme conjugate solution in 180 µL of Enzyme Immuno Assay (EIA) buffer) was added to each well. The EIA buffer is a 10 mM phosphate based buffer (pH=7.4) with Bovine Serum Albumin (BSA). The 96-well microplate was gently shaken to allow for the reagents to mix, was covered with a plastic cover and was incubated at room temperature for 60 minutes. The liquid was removed from the wells. Each well was washed three times with 300 µL of wash buffer. 150 µL of K-blue substrate was added to each well, and the plate was allowed to incubate at room temperature for 30 minutes. The K-blue substrate solution is composed of stabilized 3, 3',5,5'-tetramethylbenzidine (TMB) and hydrogen peroxide. The enzyme reaction was stopped by adding 50 µL of Neogen's Red stop solution to each well. After mixing gently, the absorbance was read with the microplate reader at 650 nm. All assays were performed in duplicate. Table 2 summarizes the results obtained with the ELISA assays. A positive result (low absorbance, which signifies that an analyte is detected) is denoted by +. A "−" sign indicates that no antibody substrate is detected. The gray shades reflect the intensity of the response: the darker the shade the more intense the response.

TABLE 2

| Fraction Number | Start Time (min) | ELISA |
|---|---|---|
| 1 | 0.0 | − |
| 2 | 1.5 | − |
| 16 | 22.5 | − |
| 17 | 24.0 | + |
| 18 | 25.5 | + |
| 19 | 27.0 | − |
| 59 | 87.0 | − |
| 60 | 88.5 | − |
| 61 | 90.0 | + |
| 62 | 91.5 | + |
| 63 | 93.0 | + |
| 64 | 94.5 | + |
| 65 | 96.0 | + |
| 66 | 97.5 | + |
| 67 | 99.0 | − |
| 96 | 142.5 | − |

The ELISA results are summarized on FIG. 15. The absorbance (at 650 nm) read for each well of the microplate was plotted against the fraction (well) number (Graph 15a). In Graph 15b, the fraction numbers were deconvoluted to time. Each fraction was assigned the time when collection of the fraction started. For example, fraction #1 was assigned time=0 min, fraction #2 was assigned time=1.5 min, etc . . . Finally, [1.6-absorbance] was plotted against Time (Graph 15c) so that the presence of a compound testing positive in the assay is visualized by a peak.

The ELISA profile indicated that activity was detected around 24 minutes and 93 minutes.

Mass spectrometry detection of the compounds allowed co-eluting peaks to be identified based on mass/charge. The activity profile demonstrates that the target compound has several obvious co-eluting compounds on the $^{ester}$IAM.PE$^{C10/C3}$ column (FIG. 13a) and very low signal intensity on the $^{ester}$IAM.PS$^{C10/C3}$ column (FIG. 13b) for late eluting compounds. There were 6 compounds in the complex mixture that overlapped with the target on the $^{ester}$IAM.PS$^{C10/C3}$ column (insert to FIG. 13b). The list of the compounds co-eluting with the Haloperidol activity on either IAM.PE or IAM.PS is given in Table 3.

TABLE 3

| Item | Cpd Name | m/z | IAM.PE tr (min) | IAM.PS tr (min) |
|---|---|---|---|---|
| 1 | loxapine | 328 | 42.36 | 87.22 |
| 2 | mianserin | 265 | 41.01 | 87.49 |
| 3 | chloroquine | 320 | 16.61 | 88.8 |
| 4 | benzydamine | 310 | 26.73 | 89.11 |
| 5 | haloperidol | 376 | 26.2 | 92.58 |
| 6 | naftopidil | 393 | 58.06 | 109.44 |
| 7 | oxybutynin | 358 | 59.76 | 121.38 |
| 8 | trihexyphenidyl | 302 | 24.26 | 81.9 |
| 9 | diltiazem | 415 | 24.83 | 50.09 |
| 10 | doxepin | 280 | 24.86 | na |
| 11 | phenyltoloxamine | 256 | 27.12 | na |
| 12 | tropine3,5dichlorobenzoate | 314 | 28.4 | na |

Single ion chromatograms (compound fingerprints) on the two IAM surfaces were obtained from the total ion chromatograms shown in FIGS. 13a and 13b for each compound of the compounds listed in Table 3. Each compound chromatographic fingerprint was compared to the activity profile to identify which compound(s) was (were) responsible for the activity. As demonstrated in FIG. 16, comparing the activity profile to the profiles of Haloperidol and Chloroquine clearly shows that the activity should be assigned to Haloperidol. No additional chromatographic runs are needed to make the prediction. FIG. 16 demonstrates that the volume of the pooled chromatography fractions affects the activity profile. For instance, 1.5 min pooled fractions were collected to obtain the data in FIG. 16 and there are only 2 fractions (~2.5–3 mL) from the $^{ester}$IAM.PE$^{C10/C3}$ column with activity. Collecting smaller fractions or concentrating the sample prior to ELISA analysis would have resulted in more active fractions. More active fractions may have resulted in the active fractions in the $^{ester}$IAM.PS$^{C10/C3}$ column to correctly identify the compound. Note that the sensitivity of the assay throughout the fractions is not constant due to the use of a flow rate gradient. Early fractions (0 to 10 min) are smaller (0.5 mL/min) than late fractions (30 min and beyond), which collect 4 nL of eluent per minute.

FIG. 17 demonstrates the importance of comparing the noise from the activity profile pattern to the detector sensitivity of the compound profile. The large background in the ELISA activity assay, and the large volume fractions sample number, causes noise in the activity profile on the $^{ester}$IAM.PS$^{C10/C3}$ column and Benzydamine can not be discriminated from Haloperidol. In spite of the overlap on the IAM.PE column, small sample volumes, i.e., more fractions, may have resulted in the assignment of activity to Haloperidol in FIG. 17. Similarly, smaller fraction size may be required to unambiguously rule out Doxepin, Phenyltoloxamine, and Tropine-3,5-dichlorobenzoate (with tr on IAM.PE very close to that of Haloperidol) as the active compounds.

C. Multiple ELISA Experiment

The objective of the experiment was to demonstrate how a compound mixture may be screened for multiple activities using the present invention. The sample mixture was composed of 7 drugs, which are listed in Table 4. Table 4 also indicates which ELISA assay each compound is expected to test positive for, based on their structural and chemical features, which are shown on FIG. 18. Also listed in Table 4 are the mass to charge ratios (m/z) characteristic of each compound for MS detection and identification.

TABLE 4

| Drug Name | Pharmaceutical Use | Molecular Target | ELISA Assay (expected results) | m/z |
|---|---|---|---|---|
| Diazepam | Tranquilizer Sedative | GABA Receptor Agonist | Benzodiazepine | 285 |
| Haloperidol | Tranquilizer-Antispychotic | Dopamine Receptor | Haloperidol | 376 |
| Hydroxyzine | Tranquilizer | Histamine H1 Receptor Antagonist | N/A | 375 |
| Imipramine | Antidepressant | 5-HT Reuptake Inhibitor | Tricyclic | 281 |
| Orphenadrine | Muscle Relaxant | N/A | N/A | 181 |
| Oxyphencyclimine | Antiulcer agent Antispasmodic | Muscarine Receptor | N/A | 345 |
| Propafenone | Ventricular & supraventricular arrhythmias | b-Adrenergic Receptor Antagonist | N/A | 342 |

The sample solution (0.6 μg/μL total concentration in 0.01M PBS buffer containing 30% DMSO) containing the 7 test compounds (~0.086 μg/μL per compound) was injected (sample loop 20 μL) on an $^{ester}$IAM.PE$^{C10/C3}$ column. The mobile phase was delivered into the LC according to the flow gradient profile described on FIG. 10b. Fractions were collected at 1.5 mm intervals (FIGS. 14 and 19). The chromatographic run was stopped after 40 minutes (27 fractions), when the last compound (Hydroxyzine) eluted from the column. The chromatographic profile is shown on FIG. 19a. There was substantial overlap between the compounds. For example Diazepam overlapped with Oxyphencyclimine and Orphenadrine. Haloperidol overlapped with Propafenone. And Imipramine overlapped with Hydroxyzine.

A second chromatographic run on a different surface was necessary to obtain a distinct chromatographic fingerprint for each compound. The sample mixture was run on an $^{ester}$IAM.PS$^{C10/C3}$ column using the same conditions described above. Fractions were collected every 1.5 minutes. The chromatographic run was stopped after 147 minutes (96 fractions), when the last compound (Propafenone) eluted from the column. The chromatographic profile is shown on FIG. 19b. All the compounds were resolved on IAM.PS surface, except for Orphenadrine and Oxyphencyclimine which completely overlapped.

Note that each chromatogram taken individually does not resolve all the compounds at once. However, the combination of the chromatographic runs on IAM.PE and IAM.PS results in 7 distinct chromatographic fingerprints, characteristic of each compound, as shown on FIG. 20. No further chromatographic run was necessary. Note that the chromatographic fingerprints of Orphenadrine and Oxyphencyclimine on IAM.PE and IAM.PS are very similar. However, they can be distinguished by their elution time on IAM.PE. Oxyphencyclimine elutes at 20 minutes, while Orphenadrine elutes at 21.5 minutes. An additional chromatographic run, or a smaller fraction size would have helped distinguish these two compounds more easily.

The series of 96 fractions for the ELISA assay was created by taking and combining aliquots (150 µL) from the fractions collected for each chromatographic run. In contrast to experiment B $^{Assay}$fractions 28 through 96 were generated by only taking an aliquot (150 µL) of each fraction from the IAM.PS chromatographic run (they were not diluted with mobile phase). Each $^{Assay}$fraction was assayed for Benzodiazepine compounds, tricyclic compounds, and Haloperidol using three different ELISA tests. The $^{Assay}$fractions were not diluted and were assayed as such.

The ELISA tests were conducted as described in experimental section B. All assays were performed in duplicate. Positive and negative controls were performed (results not shown). Table 5 summarizes the results obtained with the ELISA assays. A positive result (low absorbance, which signifies that an analyte is detected) is denoted by +. A "−" sign indicates that no antibody substrate is detected. The gray shades reflect the intensity of the response: the darker the shade the more intense the response.

TABLE 5

| Fraction Number | Start Time (min) | ELISA Benzodiazepine | ELISA Haloperidol | ELISA Tricyclic |
|---|---|---|---|---|
| 1 | 0.0 | − | − | − |
| 2 | 1.5 | − | − | − |
| 3 | 3.0 | − | − | − |
| 10 | 13.5 | − | − | − |
| 11 | 15.0 | − | − | − |
| 12 | 16.5 | − | − | − |
| 13 | 18.0 | − | − | + |
| 14 | 19.5 | + | − | + |
| 15 | 21.0 | + | − | + |
| 16 | 22.5 | + | + | − |
| 17 | 24.0 | − | + | − |
| 18 | 25.5 | − | + | − |
| 19 | 27.0 | − | + | − |
| 20 | 28.5 | − | + | + |
| 21 | 30.0 | − | − | + |
| 22 | 31.5 | − | − | + |
| 23 | 33.0 | − | − | − |
| 36 | 52.5 | − | − | − |
| 37 | 54.0 | − | − | + |
| 38 | 55.5 | − | − | + |
| 39 | 57.0 | − | − | + |
| 40 | 58.5 | − | − | + |
| 41 | 60.0 | − | − | + |
| 42 | 61.5 | − | − | − |
| 55 | 81.0 | − | − | − |
| 56 | 82.5 | − | + | − |
| 57 | 84.0 | − | + | − |
| 58 | 85.5 | − | + | − |
| 59 | 87.0 | − | + | − |
| 60 | 88.5 | − | + | − |
| 61 | 90.0 | − | + | − |
| 62 | 91.5 | − | + | − |
| 63 | 93.0 | − | + | − |
| 64 | 94.5 | − | + | − |

The ELISA results are summarized on FIG. 21. The absorbance read for each well of the microplate was plotted against the fraction number (well number) (Graphs 21a, 21d, and 21g). In Graphs 21b, 21e, and 21h, the fraction numbers were deconvolted to time. Each fraction was assigned the time when collection of the fraction started. For example, fraction #1 was assigned time=0 min, fraction #2 was assigned time=1.5 min, etc . . . Finally, [n-absorbance] was plotted against Time [see Graphs 21c (n=1), 21f (n=1.6), and 21i (n=1.1)] so that the presence of a compound testing positive in the assay is visualized by a peak. The ELISA profiles (Graphs 21c, 21f, and 21i) were compared to the chromatographic fingerprints (FIG. 20) of each of the 7 compounds in the mixture. Note that the ELISA assays appear to be more sensitive than the MS detection. This is exemplified by the fact that the ELISA peaks are in general wider and more intense, for some compounds, that the chromatographic peaks (MS detector). The response in an ELISA assay is determined by the concentration/amount of compound in the sample solution, in addition to the affinity of the test compound for the antibody deposited on the microplate. Note that the sensitivity of the assay throughout the $^{assay}$fractions is not consistent, since $^{assay}$fractions 1 through 27 are diluted two fold compared to the rest of the $^{assay}$fractions. This is because $^{assay}$fractions 1 to 27 contain equal volumes of the fractions from the IAM.PE and IAM.PS runs, while $^{assay}$fractions 28 through 96 are aliquots from the IAM.PS fractions only. In addition, early fractions (0 to 10 min) are smaller (0.5 mL/min) than late fractions (30 min and beyond), which collect 4 mL of eluent per minute. As a result, the sensitivity of the ELISAs increases across the fractions. In MS detection, the signal intensity depends not only on the concentration of the sample, but also on the ionization efficiency of the analyte. In this case all 7 compounds are present in the sample mixture in strictly the same concentration (0.086 µg/µL per compound or 0.6 µg/µL total sample mixture concentration). However, due to their different structures and chemical functionalities, the test compounds do not have the same ionization efficiency. If the test compounds exhibited similar ionization efficiencies, the chromatograms would comprise 7 peaks of similar area under the curve. This is not the case. Consequently, the peak widths for chromatographic peaks and ELISA peaks do not exactly match (particularly for lower ionization efficiency compounds), but the peak positions (time of elution) are identical, which is a sufficient condition for the purpose of the proposed invention.

As shown on FIG. 22, the Benzodiazepine ELISA fingerprint matches the chromatographic profile of Diazepam. The "Benzodiazepine activity" is detected in wells/fractions 14 and 15, which correspond to an elution time of 19.5–22.5 minutes. Only the chromatographic fingerprint of Diazepam matches this profile (FIG. 20). The conclusion from this finding is that one compound in the sample mixture is detected by the Benzodiazepine ELISA assay, and that this compound is identified as being Diazepam. This is consistent with the fact that Diazepam is the only compound in the test mixture that belongs to the Benzodiazepine family.

Similarly, comparison of the ELISA profile for the Haloperidol test only matches the chromatographic fingerprint of Haloperidol (FIG. 22).

Unexpectedly, the ELISA fingerprint for the tricyclic compounds assay revealed that two compounds in the mixture were detected by the "tricyclic antibody". As shown on FIG. 23, the ELISA fingerprint matched the summation/superimposition of two chromatographic fingerprints: that of Imipramine and a second compound, which could be Oxyphencyclimine or Orphenadrine. ELISA activity was present in fractions 14 and 15 (19.5 to 21 minutes). This was consistent with the elution profile of Oxyphencyclimine (tr=20 min), not Orphenadrine which elutes at 21.5 minutes. However, smaller fraction size may have made the assignment more clear. We anticipated that only Imipramine would test positive in the tricyclic ELISA test, since its chemical structure matched the structures that are typically recognized/detected in this test (FIGS. 11 and 18). Oxyphencyclimine was not expected to be detected since it does not have the structural features that the tricyclic ELISA test is known to recognize.

Thus the experiment described above exemplifies how the present invention may find utility in screening complex mixtures of compounds for multiple activities. The unique set of fractions collected after at least two chromatographic runs (using different sets of separation parameters each time) may be assayed for multiple properties.

Other Example of Experimental Design

The search for an effective chemotherapeutic treatment against human immunodeficiency virus (HIV) infection has lead to the development of agents that target specific and critical events in the HIV replicative cycle. The identification of compounds active against the reproduction of HIV involves the selection of a method (assay) for the discovery of the activity, and also the acquisition of materials to be tested as well.

As an example of how the present invention may be useful for the discovery of new therapeutic agents for the treatment of AIDS, outlined below is an example of experimental design that would demonstrate the efficient detection of anti-HIV compound(s) in a complex mixture of drugs. Table 6 is a partial list of drugs belonging to different therapeutic classes that may be included in the sample mixture for assessment for anti-viral activity, according to the screening method described in the present invention. At least one of the test drugs in the sample mixture has anti-viral properties (for example: AZT or Zidovudine). The present invention would allow to unequivocally detect the presence of a reverse transcriptase inhibitor (such as AZT) in a sample mixture containing 50 to 100 compounds after two or more chromatographic runs. The sample drugs may be chromatographically evaluated on IAM columns using a normal one-column HPLC system. The sample drugs discussed in this section (and listed in Table 6 below) are compounds that have significant overlap when chromatographed on an $^{ester}$IAM.PC$^{C10/C3}$, and illustrate the problem of obtaining distinct chromatographic fingerprints for each of the compounds in the test mixture.

TABLE 6

| DrugName | IAM.PC (αk') | IAM.PE (αk') | IAM.PS (αk') | IAM.SM (αk') |
| --- | --- | --- | --- | --- |
| AZT | 0.36 | 0.76 | 0.36 | 0.26 |
| Mescaline | 0.62 | 1.95 | 11.39 | 0.49 |
| Nikethamide | 0.33 | 1.55 | 0.61 | 0.30 |
| Norfloxacin | 0.64 | 1.31 | 8.09 | 2.09 |
| Olazoline | 0.52 | 1.19 | 4.72 | 0.49 |

Sample Preparation

The samples may be dissolved in the mobile phase. If a sample does not dissolve well in the mobile phase, adjustments may be made. For instance, a small amount of more polar or non-polar solvent may be used. The concentration of sample solution can be 0.1 $\mu$mol/$\mu$L.

Experimental Conditions for the HPLC System

Dimensions of the columns: 3.0×0.46 cm.
Sample amount: 20 $\mu$L.
LC flow rate: 1 mL/min.
Wavelength of the UV detector: 220 nm.
Mobile phase composition: 15% of acetonitrile+85% of 0.03 M NH$_4$OAc buffer (pH 7.4).

All five compounds were chromatographed on $^{ester}$IAM.PC$^{C10/C3}$, $^{ester}$IAM.PE$^{C10/C3}$, $^{ester}$IAM.PS$^{C10/C3}$, IAM.SM$^{C10/C3}$ using the experimental conditions described above. A representative set of normalized capacity factor values (αk') of these drugs are presented in Table 6 [It should be noted that these values are very much dependent on packing material quality and density, as well as mobile phase composition (particularly the pH). Thus these values are not absolute and may vary from column to column within the same column type].

The eluting order of these drugs on IAM.PC is given by their respective capacity factors, and is depicted on FIG. 24a. A sample solution made up of 50 to 100 compounds including all five drugs listed in Table 6 may be run on an $^{ester}$IAM.PC$^{C10/C3}$ column and the eluent may be collected in a series of fractions at fixed time or volume intervals. The early portion of the resulting chromatogram is expected to resemble that depicted on FIG. 25a, with substantial overlap between the compounds listed in Table 6. In its first iteration the algorithm should determine that there is substantial overlap between the peaks, and that an additional LC/MS run on a different column (for example IAM.PE) is necessary. The eluting order of the five drugs listed in Table 6 on an $^{ester}$IAM.PC$^{C10/C3}$ column is exemplified on FIG. 24b. The early portion of the chromatogram of the sample mixture on IAM.PE is expected to look like that shown on FIG. 25b. At this point, the chromatographic fingerprints for all five drugs are distinct enough that the algorithm will determine that the chromatographic patterns are unique and suited for bioassay screening (FIG. 26). If the same is true for the rest of the 50–100 compounds in the test mixture, no additional chromatographic run should be necessary. The series of combined fractions could then be lyophilized (concentrated) and prepared for anti-viral activity evaluation. Most likely, an ELISA-type assay would be suitable for this purpose, but other types of assays are available.

There are two general types of methods used in AIDS drug discovery, which are "mechanistic" assays and general biological or "cell-based" assays. General biological assays (or cell-based assays) recognize compounds that might be active at any stage of virus reproduction, whereas the mechanistic assays typically are designed to identify compounds which affect a particular component in the virus reproductive cycle.

The following is an outline of the different types of assays in each category.

Mechanism-based Assays for the Discovery of Antiviral Compounds gp120-CD4 binding assay.
Reverse transcriptase assay.
Integrase assay.
p7 Nucleocapsid protein zinc finger assay.
Protease assay.
Cell-based screens for the discovery of antiviral compounds.
Cytoprotection and viral replication screening assays.
Nonhazardous screening assay.
Other cell-based screening assays.

Several types of assay are currently used to elucidate the determination of the mechanism of action of antiviral compounds.

Time-Course Assay

In this procedure the target cells (10$^5$ CEM-SS cells) are preincubated with a cytopathic strain of HIV-1 (IIIb strain at a high multiplicity of infection, MOI=1) at 0–4° C. for 1 hr to allow attachment of virus to cells. This low temperature precludes progression to fusion or reverse transcription. The unbound virus is washed away, and at the nominal start of the experiment ($t_0$) the samples are rapidly warmed to 37° C. allowing the infection cycle to proceed. Test compounds are included during the preincubation step only (Pre), during the preincubation with re-addition at $t_0$ (Pre/$t_0$) following removal of the free virus, or added to samples only at $t_0$ or at various times after warming to 37° C. After 24 hr in culture tubes, each sample is divided for two separate types of evaluation. An equivalent of $5 \times 10^3$ cells from each sample is prepared in triplicate and cultured for an additional 72 hr in 96-well plates, after which they are analyzed for XTT cytoprotection and virion-associated p24 production. The remaining portion of the samples in the culture tubes at the 24 hr incubation point are collected and the cells are analyzed by PCR methodology. Full-length reverse transcripts are detected using primer pairs that amplify the LTR/gag region of HIV-1 proviral DNA, and the presence of such transcripts indicates that reverse transcription has been completed.

Virus Replication Inhibition Assays

Typically, Phytohemagglutinin-stimulated human peripheral blood mononuclear cells (PBMCs) are distributed into 96-well plates ($10^5$ per well) in the presence of the indicated concentrations of tested compound and 250 50% tissue culture infectious doses ($TCID_{50}$) of the HIV-1$_{WeJo}$ pediatric clinical isolate, which has been propagated only in human PBMCs. After 7 days, cultures are assayed for p24 antigen content with a p24 antigen-capture kit. Cell viability is quantitated by using biscarboxyethyl-5(6)-carboxyfluorescein acetoxymethyl ester.

Binding Assays

The binding of gp120 to CD4 may be analyzed using an antigen capture ELISA. The effects of drugs on the in vitro activity of purified RT can be determined by measurement of incorporation of [$^3$H]TTP onto the artificial poly(rA):oligo (dT)homopolymer primer/template. Samples (5 µL) are blotted onto DE81 paper, washed with 5% dibasic sodium phosphate and then quantitated on a Packard Matrix 9600 direct beat counter.

Reverse Transcriptase and Protease Assays

The in vitro activity of reverse transcriptase can be determined with an ELISA kit and with 3'-azido-3'-deoxythmidine-5'-triphosphate (AZTTP) serving as a positive control for inhibition of reverse transcriptase. For assay of endogenous reverse transcription, 10 µg of HIV-1$_{HIB}$ was treated with tested compound at the defined concentrations for 10 min at 25° C., followed by permeabilization of the virus with melittin and subsequent incubation of the reaction mixture without dithiothreitol for 6 hr at 39° C. Reactions are terminated with 0.1% SDS/10 mM EDTA, electrophoresis was preformed with 0.7% agarose gels, and the gels are dried and exposed for autoradiograph. HIV-1 protease activity is quantitated by a reverse-phase HPLC assay, but without dithiothreitol.

Integrase Assay

An example of integrase assay procedure is as follows. The integrase stock enzyme (0.44 mg/mL) is diluted 1:3 in protein storage buffer 1 M NaCl/20 mM Hepes, pH 7.6/1 mM dithiothreitol/20% (wt/vol) glycerol. Subsequent enzyme dilution is at 1:20 in reaction buffer (25 mM mops, pH 7.2/7.5 mM $MnCl_2$/bovine serum albumin at 100 µg/mL/10 mM 2-mercaptoethanol) to give 50 mM NaCl/1 mM Hepes/50 µM EDTA/50 µM dithiothreitol/10% (wt/vol) glycerol/7.5 mM $MnCl_2$/bovine serum albumin at 0.1 mg/mL/10 mM 2-cercaptoethanol/25 mM Mops, pH 7.2. The reaction volume is 16 µL. Reactions are typically run for 1 hr with 0.3 pmol of $^{32}$P-labeled double-stranded oligonucleotide. Reactions are stopped by adding 16 µL of Maxarn-Gilbert loading buffer to each 16 µL sample. Subsequently 4 µL of each sample is run on a 20% denaturing polyacrylamide gel in 1×TBE buffer (TBE is 90 mM Tris/64.6 mM boric acid/2.5 mM EDTA, pH 8.3). The gels are dried, and subjected to autoradiography.

We claim:

1. A method of identifying one or more compounds having a predetermined characteristic in a complex compound mixture, said method comprising
    (a) subjecting said compound mixture to a separation process using a first set of compound separation parameters to at least partially separate the compounds in the mixture into a series of separation variable-dependent fractions (Fa) in the order Fa1, Fa2, Fa3, . . . Fan wherein n is the number of fractions collected using said first set of separation variables, at least a portion of which fractions include one or more compounds of the compound mixture;
    (b) repeating step (a) using a second unique set of separation parameters to produce a second series of separation parameter-dependent fractions (Fb) in the order Fb1, Fb2, Fb3, . . . Fbm wherein m is the number of fractions collected using the second set of separation parameters;
    (c) combining each of the qth fractions obtained using each set of separation parameters, wherein q is the respective order number of the fractions obtained using each set of separation parameters, to provide combined qth fractions:
    (d) obtaining spectral data on compound components of each of said combined fractions, said data being characteristic of the compound or compounds in the combined fractions;
    (e) analyzing each combined fraction to detect the presence of the predetermined chemical, physical or biological characteristic and identifying each of those combined fractions that exhibit the predetermined characteristic;
    (f) comparing the spectral data for each of the combined fractions exhibiting the predetermined characteristic to identify spectral data common to each of said combined fractions that exhibit the predetermined characteristics; and
    (g) identifying the compound or compounds characterized by the spectral data common to the combined fractions exhibiting the predetermined characteristic in said combined fractions.

2. The method of claim 1 wherein step (a) is repeated at least one additional time using a third unique set of separation parameters to produce a third series of separation-variable dependent fractions.

3. The method of claim 1 wherein the spectral data are selected from mass spectral data, infrared spectral data, ultraviolet spectral data, and nuclear magnetic resonance spectral data.

4. The method of claim 3 wherein the spectral data are recorded for the compound components in each fraction obtained using each set of separation variables and the step of obtaining spectral data on the compound components of each of said combined fractions is carried out by combining the spectral data of thee compounds in the component fractions.

5. The method of claim 4 wherein the separation process is chromatographic and the spectral data are recorded for each eluted compound as the compound is detected during elution from the chromatographic system.

6. The method of claim 1 wherein the compound mixture is a combinatorial chemical library, a natural product extract, or other extracts derived from any living system.

7. The method of claim 1 wherein the separation process is chromatography and said set of separation parameters is selected from the group consisting of solid phase, mobile phase, flow rate, and gradients thereof, and temperature.

8. The method of claim 1 wherein the complex mixture of compounds is subjected to a separation process comprising high pressure liquid chromatography.

9. The method of claim 1 wherein the predetermined characteristic is a biological property.

10. The method of claim 1 wherein the predetermined characteristic is a physical property.

11. The method of claim 1 wherein the predetermined characteristic is a chemical property.

12. The method of claim 1 wherein the predetermined characteristic is toxicity.

13. The method of claim 1 wherein the predetermined characteristic is a specific binding property.

14. The method of claim 1 wherein the complex mixture comprises proteins or digests thereof.

* * * * *